(12) United States Patent
Spence et al.

(10) Patent No.: US 12,263,081 B2
(45) Date of Patent: Apr. 1, 2025

(54) APPARATUS AND METHODS FOR IMPLANTING A REPLACEMENT HEART VALVE

(71) Applicant: Mitral Valve Technologies Sarl, Nyon (CH)

(72) Inventors: Paul A. Spence, Louisville, KY (US); Landon H. Tompkins, Peachtree Corners, GA (US)

(73) Assignee: Mitral Valve Technologies Sarl, Nyon (CH)

( * ) Notice: Subject to any disclaimer, the term of this patent is extended or adjusted under 35 U.S.C. 154(b) by 11 days.

(21) Appl. No.: 18/465,137

(22) Filed: Sep. 11, 2023

(65) Prior Publication Data
US 2023/0414345 A1  Dec. 28, 2023

Related U.S. Application Data

(60) Continuation of application No. 17/197,574, filed on Mar. 10, 2021, now Pat. No. 11,793,630, which is a continuation of application No. 15/992,535, filed on May 30, 2018, now Pat. No. 10,945,837, which is a division of application No. 14/911,539, filed as
(Continued)

(51) Int. Cl.
*A61F 2/24* (2006.01)
*A61F 2/88* (2006.01)

(52) U.S. Cl.
CPC ............ *A61F 2/2409* (2013.01); *A61F 2/243* (2013.01); *A61F 2/2412* (2013.01); *A61F 2/2418* (2013.01); *A61F 2/2433* (2013.01); *A61F 2/88* (2013.01); *A61F 2210/0014* (2013.01); *A61F 2220/0016* (2013.01); *A61F 2230/0008* (2013.01); *A61F 2230/0091* (2013.01); *A61F 2250/001* (2013.01); *A61F 2250/0036* (2013.01); *A61F 2250/0039* (2013.01); *A61F 2250/0048* (2013.01); *A61F 2250/006* (2013.01); *A61F 2250/0069* (2013.01)

(58) Field of Classification Search
CPC ........ A61F 2/2409; A61F 2/2442–2448; A61F 2210/0061; A61F 2250/0069–007
See application file for complete search history.

(56) References Cited

U.S. PATENT DOCUMENTS

| 30,912 A | 12/1860 | Hancock |
|---|---|---|
| 3,409,013 A | 11/1968 | Berry |
| 3,548,417 A | 12/1970 | Kisher |

(Continued)

FOREIGN PATENT DOCUMENTS

| CN | 1714766 A | 1/2006 |
|---|---|---|
| CN | 102389341 A | 3/2012 |

(Continued)

OTHER PUBLICATIONS

Machine translation of FR3004335A1. (Year: 2024).*

*Primary Examiner* — Rebecca S Preston
(74) *Attorney, Agent, or Firm* — Klarquist Sparkman, LLP; Linda Allyson Nassif

(57) ABSTRACT

Anchors and systems for docking a prosthetic heart valve at a native heart valve are disclosed. An anchor can include at least three coils and a covering extending over at least a portion of the at least three coils. The covering comprises a fabric material and a foam underneath the fabric material.

18 Claims, 27 Drawing Sheets

Related U.S. Application Data application No. PCT/US2014/050525 on Aug. 11, 2014, now Pat. No. 10,034,749.

(60) Provisional application No. 61/878,280, filed on Sep. 16, 2013, provisional application No. 61/867,287, filed on Aug. 19, 2013, provisional application No. 61/864,860, filed on Aug. 12, 2013.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,666,442 A | 5/1987 | Arru et al. |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,599,305 A | 2/1997 | Hermann et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,379,372 B1 | 4/2002 | Dehdashtian et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |

(56) References Cited

U.S. PATENT DOCUMENTS

| | | |
|---|---|---|
| 6,936,067 B2 | 8/2005 | Buchanan |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,096,554 B2 | 8/2006 | Austin et al. |
| 7,101,395 B2 | 9/2006 | Tremulis et al. |
| 7,125,421 B2 | 10/2006 | Tremulis et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 7,959,661 B2 | 6/2011 | Hijlkema et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,128,691 B2 | 3/2012 | Keranen |
| 8,167,932 B2 | 5/2012 | Bourang et al. |
| 8,291,570 B2 | 10/2012 | Eidenschink et al. |
| 8,323,335 B2 | 12/2012 | Rowe et al. |
| 8,348,998 B2 | 1/2013 | Pintor et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,734,507 B2 | 5/2014 | Keranen |
| 8,747,463 B2 | 6/2014 | Fogarty et al. |
| 9,078,747 B2 | 7/2015 | Conklin |
| 9,078,781 B2 | 7/2015 | Ryan et al. |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,622,863 B2 | 4/2017 | Karapetian et al. |
| 9,867,702 B2 | 1/2018 | Keränen et al. |
| 10,195,033 B2 | 2/2019 | Tuval et al. |
| 11,020,225 B2 | 6/2021 | Keränen et al. |
| 11,039,924 B2 | 6/2021 | Yaron |
| 11,364,114 B2 | 6/2022 | Gorman, III et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173841 A1 | 11/2002 | Ortiz et al. |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0225420 A1 | 12/2003 | Wardle |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0133263 A1 | 7/2004 | Dusbabek et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075724 A1 | 4/2005 | Svanidze et al. |
| 2005/0075725 A1 | 4/2005 | Rowe |
| 2005/0075728 A1 | 4/2005 | Nguyen et al. |
| 2005/0080474 A1 | 4/2005 | Andreas et al. |
| 2005/0096736 A1 | 5/2005 | Osse et al. |
| 2005/0096738 A1 | 5/2005 | Cali et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0233062 A1* | 10/2005 | Hossainy .............. A61F 2/91 427/2.1 |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0195185 A1 | 8/2006 | Lane et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0033542 A1 | 2/2008 | Antonsson et al. |
| 2008/0109017 A1 | 5/2008 | Herweck et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0208330 A1 | 8/2008 | Keranen |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294230 A1 | 11/2008 | Parker |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0299471 A1 | 12/2009 | Keranen |
| 2009/0319037 A1 | 12/2009 | Rowe et al. |
| 2010/0030014 A1* | 2/2010 | Ferrazzi .............. A61F 2/2445 600/37 |
| 2010/0049313 A1 | 2/2010 | Alon et al. |
| 2010/0076549 A1 | 3/2010 | Keidar et al. |
| 2010/0082094 A1 | 4/2010 | Quadri et al. |

(56) References Cited

U.S. PATENT DOCUMENTS

| | | |
|---|---|---|
| 2010/0145440 A1 | 6/2010 | Keranen |
| 2010/0168844 A1* | 7/2010 | Toomes ............... A61F 2/2418 623/2.18 |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0312333 A1 | 12/2010 | Navia et al. |
| 2010/0318184 A1 | 12/2010 | Spence |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0218621 A1 | 9/2011 | Antonsson et al. |
| 2011/0319990 A1 | 12/2011 | Macoviak et al. |
| 2011/0319991 A1 | 12/2011 | Hariton et al. |
| 2012/0016464 A1 | 1/2012 | Seguin |
| 2012/0053680 A1 | 3/2012 | Bolling et al. |
| 2012/0059458 A1 | 3/2012 | Buchbinder et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2012/0283820 A1 | 11/2012 | Tseng et al. |
| 2012/0310328 A1* | 12/2012 | Olson .................. A61F 2/2469 623/1.26 |
| 2012/0316643 A1 | 12/2012 | Keranen |
| 2013/0006352 A1 | 1/2013 | Yaron |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0190862 A1 | 7/2013 | Pintor et al. |
| 2013/0274873 A1 | 10/2013 | Delaloye et al. |
| 2013/0304197 A1 | 11/2013 | Buchbinder et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0074299 A1 | 3/2014 | Endou et al. |
| 2014/0172070 A1 | 6/2014 | Seguin |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2014/0358222 A1 | 12/2014 | Gorman, III et al. |
| 2014/0379074 A1 | 12/2014 | Spence et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2015/0230921 A1 | 8/2015 | Chau et al. |
| 2015/0282931 A1 | 10/2015 | Brunnett et al. |
| 2015/0335428 A1 | 11/2015 | Keranen |
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0256276 A1 | 9/2016 | Yaron |
| 2017/0007399 A1 | 1/2017 | Keranen |
| 2017/0007402 A1 | 1/2017 | Zerkowski et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | | |
|---|---|---|---|
| CN | 104220027 A | 12/2014 | |
| DE | 19532846 A1 | 3/1997 | |
| DE | 19907646 A1 | 8/2000 | |
| EP | 0592410 B1 | 10/1995 | |
| EP | 0850607 A1 | 7/1998 | |
| EP | 1432369 A1 | 6/2004 | |
| EP | 1521550 A2 | 4/2005 | |
| EP | 1796597 A2 | 6/2007 | |
| EP | 1296618 B1 | 1/2008 | |
| EP | 2072027 A1 | 6/2009 | |
| EP | 1827314 B1 | 12/2010 | |
| EP | 2591755 A1 | 5/2013 | |
| EP | 2620125 A1 | 7/2013 | |
| EP | 2726018 A2 | 5/2014 | |
| EP | 2806829 A2 | 12/2014 | |
| EP | 3395296 B1 | 12/2019 | |
| EP | 2747708 B1 | 1/2022 | |
| FR | 2815844 A1 | 5/2002 | |
| FR | 3004335 A1 * | 10/2014 | ........... A61F 2/2445 |
| JP | 2016529995 A | 9/2016 | |
| WO | 9117720 A1 | 11/1991 | |
| WO | 9829057 A1 | 7/1998 | |
| WO | 0149213 A2 | 7/2001 | |
| WO | 0154625 A1 | 8/2001 | |
| WO | 0176510 A2 | 10/2001 | |
| WO | 0203892 A1 | 1/2002 | |
| WO | 0222054 A1 | 3/2002 | |
| WO | 0236048 A1 | 5/2002 | |
| WO | 0247575 A2 | 6/2002 | |
| WO | 03047468 A1 | 6/2003 | |
| WO | 2005084595 A1 | 9/2005 | |
| WO | 2006011127 A2 | 2/2006 | |
| WO | 2006091163 A1 | 8/2006 | |
| WO | 2006111391 A1 | 10/2006 | |
| WO | 2006138173 A2 | 12/2006 | |
| WO | 2005102015 A3 | 4/2007 | |
| WO | 2007047488 A2 | 4/2007 | |
| WO | 2007067942 A1 | 6/2007 | |
| WO | 2008058940 A1 | 5/2008 | |
| WO | 2010121076 A2 | 10/2010 | |
| WO | 2012016464 A1 | 2/2012 | |
| WO | 2013068542 A1 | 5/2013 | |
| WO | 2013110722 A2 | 8/2013 | |
| WO | 2013114214 A2 | 8/2013 | |
| WO | 2015023579 A1 | 2/2015 | |
| WO | 2015023862 A2 | 2/2015 | |
| WO | 2015085218 A1 | 6/2015 | |
| WO | 2015127264 A1 | 8/2015 | |
| WO | 2015198125 A1 | 12/2015 | |
| WO | 2016038017 A1 | 3/2016 | |
| WO | 2016040881 A1 | 3/2016 | |
| WO | 2016130820 A1 | 8/2016 | |

* cited by examiner

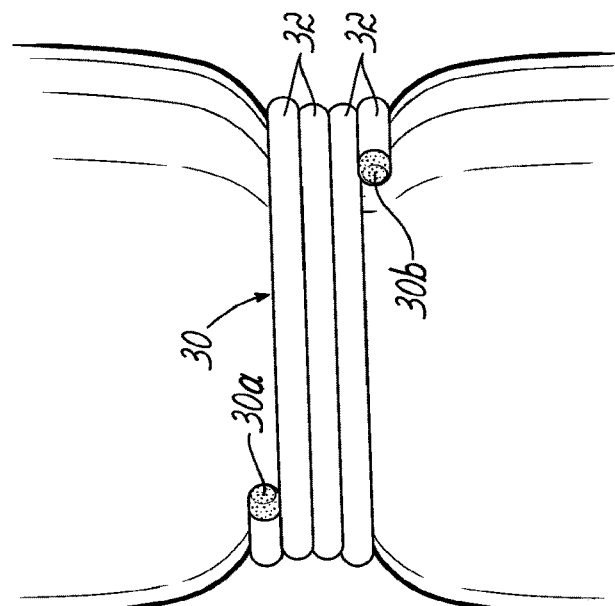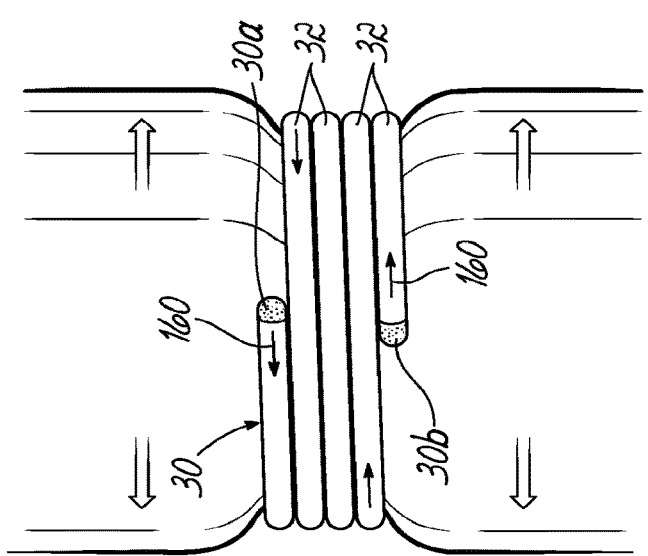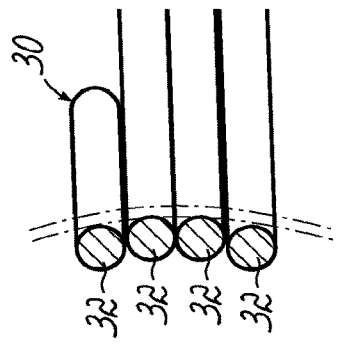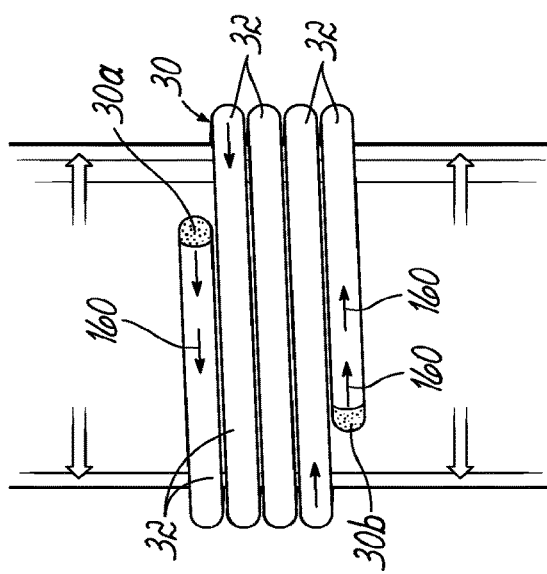
FIG. 9C
FIG. 9B
FIG. 9D
FIG. 9A

APPARATUS AND METHODS FOR IMPLANTING A REPLACEMENT HEART VALVE

CROSS-REFERENCE TO RELATED APPLICATIONS

This application is a continuation of U.S. patent application Ser. No. 17/197,574, filed Mar. 10, 2021, which is a continuation of U.S. patent application Ser. No. 15/992,535, filed May 30, 2018, now U.S. Pat. No. 10,945,837, which is a divisional of U.S. patent application Ser. No. 14/911,539, filed Feb. 11, 2016, now U.S. Pat. No. 10,034,749, which is a U.S. national phase application of PCT patent application PCT/US2014/050525, filed Aug. 11, 2014, which claims the benefit of U.S. Provisional Application Ser. No. 61/878,280, filed Sep. 16, 2013, 61/867,287, filed Aug. 19, 2013, and 61/864,860, filed Aug. 12, 2013, the disclosures of which are hereby incorporated by reference herein.

TECHNICAL FIELD

The present invention generally relates to medical procedures and devices pertaining to heart valves such as replacement techniques and apparatus. More specifically, the invention relates to the replacement of heart valves having various malformations and dysfunctions.

BACKGROUND

Complications of the mitral valve, which controls the flow of blood from the left atrium into the left ventricle of the human heart, have been known to cause fatal heart failure. In the developed world, one of the most common forms of valvular heart disease is mitral valve leak, also known as mitral regurgitation, which is characterized by the abnormal leaking of blood from the left ventricle through the mitral valve and back into the left atrium. This occurs most commonly due to ischemic heart disease when the leaflets of the mitral valve no longer meet or close properly after multiple infarctions, idiopathic and hypertensive cardiomyopathies where the left ventricle enlarges, and with leaflet and chordal abnormalities, such as those caused by a degenerative disease.

In addition to mitral regurgitation, mitral narrowing or stenosis is most frequently the result of rheumatic disease. While this has been virtually eliminated in developed countries, it is still common where living standards are not as high.

Similar to complications of the mitral valve are complications of the aortic valve, which controls the flow of blood from the left ventricle into the aorta. For example, many older patients develop aortic valve stenosis. Historically, the traditional treatment had been valve replacement by a large open heart procedure. The procedure takes a considerable amount of time for recovery since it is so highly invasive. Fortunately, in the last decade great advances have been made in replacing this open heart surgery procedure with a catheter procedure that can be performed quickly without surgical incisions or the need for a heart-lung machine to support the circulation while the heart is stopped. Using catheters, valves are mounted on stents or stent-like structures, which are compressed and delivered through blood vessels to the heart. The stents are then expanded and the valves begin to function. The diseased valve is not removed, but instead it is crushed or deformed by the stent which contains the new valve. The deformed tissue serves to help anchor the new prosthetic valve.

Delivery of the valves can be accomplished from arteries which can be easily accessed in a patient. Most commonly this is done from the groin where the femoral and iliac arteries can be cannulated. The shoulder region is also used, where the subclavian and axillary arteries can also be accessed. Recovery from this procedure is remarkably quick.

Not all patients can be served with a pure catheter procedure. In some cases the arteries are too small to allow passage of catheters to the heart, or the arteries are too diseased or tortuous. In these cases, surgeons can make a small chest incision (thoracotomy) and then place these catheter-based devices directly into the heart. Typically, a purse string suture is made in the apex of the left ventricle and the delivery system is place through the apex of the heart. The valve is then delivered into its final position. These delivery systems can also be used to access the aortic valve from the aorta itself. Some surgeons introduce the aortic valve delivery system directly in the aorta at the time of open surgery. The valves vary considerably. There is a mounting structure that is often a form of stent. Prosthetic leaflets are carried inside the stent on mounting and retention structure. Typically, these leaflets are made from biologic material that is used in traditional surgical valves. The valve can be actual heart valve tissue from an animal or more often the leaflets are made from pericardial tissue from cows, pigs or horses. These leaflets are treated to reduce their immunogenicity and improve their durability. Many tissue processing techniques have been developed for this purpose. In the future biologically engineered tissue may be used or polymers or other non-biologic materials may be used for valve leaflets. All of these can be incorporated into the inventions described in this disclosure.

There are in fact more patients with mitral valve disease than aortic valve disease. In the course of the last decade many companies have been successful in creating catheter or minimally invasive implantable aortic valves, but implantation of a mitral valve is more difficult and to date there has been no good solution. Patients would be benefited by implanting a device by a surgical procedure employing a small incision or by a catheter implantation such as from the groin. From the patient's point of view, the catheter procedure is very attractive. At this time there is no commercially available way to replace the mitral valve with a catheter procedure. Many patients who require mitral valve replacement are elderly and an open heart procedure is painful, risky and takes time for recovery. Some patients are not even candidates for surgery due to advanced age and frailty. Therefore, there exists a particular need for a remotely placed mitral valve replacement device.

While previously it was thought that mitral valve replacement rather than valve repair was associated with a more negative long term prognosis for patients with mitral valve disease, this belief has come into question. It is now believed that the outcome for patients with mitral valve leak or regurgitation is almost equal whether the valve is repaired or replaced. Furthermore, the durability of a mitral valve surgical repair is now under question. Many patients, who have undergone repair, redevelop a leak over several years. As many of these are elderly, a repeat intervention in an older patient is not welcomed by the patient or the physicians.

The most prominent obstacle for catheter mitral valve replacement is retaining the valve in position. The mitral valve is subject to a large cyclic load. The pressure in the left ventricle is close to zero before contraction and then rises to the systolic pressure (or higher if there is aortic stenosis) and this can be very high if the patient has systolic hypertension. Often the load on the valve is 150 mm Hg or more. Since the heart is moving as it beats, the movement and the load can combine to dislodge a valve. Also the movement and rhythmic load can fatigue materials leading to fractures of the materials. Thus, there is a major problem associated with anchoring a valve. Another problem with creating a catheter delivered mitral valve replacement is size. The implant must have strong retention and leak avoidance features and it must contain a valve. Separate prostheses may contribute to solving this problem, by placing an anchor or dock first and then implanting the valve second. However, in this situation the patient must remain stable between implantation of the anchor or dock and implantation of the valve. If the patient's native mitral valve is rendered non-functional by the anchor or dock, then the patient may quickly become unstable and the operator may be forced to hastily implant the new valve or possibly stabilize the patient by removing the anchor or dock and abandoning the procedure.

Another problem with mitral replacement is leak around the valve, or paravalvular leak. If a good seal is not established around the valve, blood can leak back into the left atrium. This places extra load on the heart and can damage the blood as it travels in jets through sites of leaks. Hemolysis or breakdown of red blood cells is a frequent complication if this occurs. Paravalvular leak was one of the common problems encountered when the aortic valve was first implanted on a catheter. During surgical replacement, a surgeon has a major advantage when replacing the valve as he or she can see a gap outside the valve suture line and prevent or repair it. With catheter insertion, this is not possible. Furthermore, large leaks may reduce a patient's survival and may cause symptoms that restrict mobility and make the patient uncomfortable (e.g. short of breathe, edematous, fatigued). Therefore, devices, systems, and methods which relate to mitral valve replacement should also incorporate means to prevent and repair leaks around the replacement valve.

A patient's mitral valve annulus can also be quite large. When companies develop surgical replacement valves, this problem is solved by restricting the number of sizes of the actual valve produced and then adding more fabric cuff around the margin of the valve to increase the valve size. For example, a patient may have a 45 mm valve annulus. In this case, the actual prosthetic valve diameter may be 30 mm and the difference is made up by adding a larger band of fabric cuff material around the prosthetic valve. However, in catheter procedures, adding more material to a prosthetic valve is problematic since the material must be condensed and retained by small delivery systems. Often this method is very difficult and impractical, so alternative solutions are necessary.

Since numerous valves have been developed for the aortic position, it is desirable to avoid repeating valve development and to take advantage of existing valves. These valves have been very expensive to develop and bring to market, so extending their application can save considerable amounts of time and money. It would be useful then to create a mitral anchor or docking station for such a valve. An existing valve developed for the aortic position, perhaps with some modification, could then be implanted in the docking station. Some previously developed valves may fit well with no modification, such as the Edwards Sapien™ valve. Others, such as the Corevalve™ may be implantable but require some modification for an optimal engagement with the anchor and fit inside the heart.

A number of further complications may arise from a poorly retained or poorly positioned mitral valve replacement prosthesis. Namely, a valve can be dislodged into the atrium or ventricle, which could be fatal for a patient. Prior prosthetic anchors have reduced the risk of dislodgement by puncturing tissue to retain the prosthesis. However, this is a risky maneuver since the penetration must be accomplished by a sharp object at a long distance, leading to a risk of perforation of the heart and patient injury.

Orientation of the mitral prosthesis is also important. The valve must allow blood to flow easily from the atrium to the ventricle. A prosthesis that enters at an angle may lead to poor flow, obstruction of the flow by the wall of the heart or a leaflet and a poor hemodynamic result. Repeated contraction against the ventricular wall can also lead to rupture of the back wall of the heart and sudden death of the patient.

With surgical mitral valve repair or replacement, sometimes the anterior leaflet of the mitral valve leaflet is pushed into the area of the left ventricular outflow and this leads to poor left ventricular emptying. This syndrome is known as left ventricular tract outflow obstruction. The replacement valve itself can cause left ventricular outflow tract obstruction if it is situated close to the aortic valve.

Yet another obstacle faced when implanting a replacement mitral valve is the need for the patient's native mitral valve to continue to function regularly during placement of the prosthesis so that the patient can remain stable without the need for a heart-lung machine to support circulation.

In addition, it is desirable to provide devices and methods that can be utilized in a variety of implantation approaches. Depending on a particular patient's anatomy and clinical situation, a medical professional may wish to make a determination regarding the optimal method of implantation, such as inserting a replacement valve directly into the heart in an open procedure (open heart surgery or a minimally invasive surgery) or inserting a replacement valve from veins and via arteries in a closed procedure (such as a catheter-based implantation). It is preferable to allow a medical professional a plurality of implantation options to choose from. For example, a medical professional may wish to insert a replacement valve either from the ventricle or from the atrial side of the mitral valve.

Therefore, the present invention provides devices and methods that address these and other challenges in the art.

SUMMARY

In one illustrative embodiment, a system for docking a heart valve prosthesis is provided and includes a helical anchor formed as multiple coils adapted to support a heart valve prosthesis with coil portions positioned above and below the heart valve annulus and a seal coupled with the helical anchor. The seal includes portions extending between adjacent coils for preventing blood leakage through the helical anchor and past the heart valve prosthesis.

The system can further include a heart valve prosthesis capable of being delivered to a native heart valve position of a patient and expanded inside the multiple coils and into engagement with leaflets of the heart valve. The seal is engaged with both the helical anchor and the heart valve prosthesis. The coils of the helical anchor may be formed of a superelastic or a shape memory material, or other suitable material. The seal may be a membrane or panel extending over at least two coils of the helical anchor. The membrane or panel is moved between an undeployed state and a deployed state, the undeployed state being adapted for delivery to a site of implantation and the deployed state being adapted for implanting the system and anchoring the heart valve prosthesis. The undeployed state may be a rolled up state on one of the coils of the helical anchor or any other collapsed state. The membrane or panel may include a support element affixed therewith, such as an internal, spring-biased wire. The seal may further include one or more seal elements carried by the helical anchor with overlapping portions configured to seal a space between adjacent coils of the helical anchor. The one or more seal elements may each include a support element such as an internal wire, which may be a spring-biased coil or other configuration, affixed therewith. The one or more seal elements may be cross sectional shape, with examples being generally circular or oblong. The one or more seal elements may each have a connecting portion affixed to one of the coils and an extension portion extending toward an adjacent coil for providing the seal function between coils.

In another illustrative embodiment a system for replacing a native heart valve includes an expansible helical anchor formed as multiple coils adapted to support a heart valve prosthesis. At least one of the coils is normally defined by a first diameter, and is expandable to a second, larger diameter upon application of radial outward force from within the helical anchor. The system further includes an expansible heart valve prosthesis capable of being delivered into the helical anchor and expanded inside the multiple coils into engagement with the at least one coil to move the at least one coil from the first diameter to the second diameter while securing the helical anchor and the heart valve prosthesis together.

As a further aspect the helical anchor may include another coil that moves from a larger diameter to a smaller diameter as the heart valve prosthesis is expanded inside the multiple coils. At least two adjacent coils of the helical anchor may be spaced apart, and the adjacent coils move toward each other as the heart valve prosthesis is expanded inside the multiple coils. The helical anchor may further includes a plurality of fasteners, and the fasteners are moved from an undeployed state to a deployed state as the at least one coil moves from the first diameter to the second, larger diameter. A seal may be coupled with the helical anchor and include portions extending between adjacent coils for preventing blood leakage through the helical anchor and past the heart valve prosthesis. The system can further include at least one compressible element on the helical anchor, the compressible element being engaged by the heart valve prosthesis as the heart valve prosthesis is expanded inside the multiple coils to assist with affixing the heart valve prosthesis to the helical anchor. The compressible element may take any of several forms, such as fabric or other soft material, or resilient, springy material such as polymer or foam. The at least one compressible element further may include multiple compressible elements spaced along the multiple coils or a continuous compressible element extending along the multiple coils. The heart valve prosthesis may further include an expansible structure including openings. The openings are engaged by the at least one compressible element as the heart valve prosthesis is expanded inside the multiple coils for purposes of strengthening the connection between the anchor and the prosthesis. The multiple coils of the helical anchor may include at least two coils that cross over each other. This system may include any feature or features of the system that uses the seal, and vice versa, depending on the functions and effects desired.

Methods of implanting a heart valve prosthesis in the heart of a patient are also provided. In one illustrative embodiment, the method includes delivering a helical anchor in the form of multiple coils such that a portion of the helical anchor is above the native heart valve and a portion is below the native heart valve. The heart valve prosthesis is implanted within the multiple coils of the helical anchor such that the heart valve prosthesis is supported by the helical anchor. A seal is positioned between at least two adjacent coils of the helical anchor and the heart valve prosthesis for preventing leakage of blood flow during operation of the heart valve prosthesis.

Positioning the seal can further comprise positioning a membrane or panel extending over at least two coils of the helical anchor. The method further includes delivering the membrane or panel in an undeployed state to the site of the native heart valve and then deploying the membrane or panel within the helical anchor, and expanding the heart valve prosthesis against the membrane or panel. The undeployed state includes a rolled up state or other collapsed state. Positioning the seal may further include positioning one or more seal elements carried by the helical anchor such that overlapping portions seal a space between adjacent coils of the helical anchor. The one or more seal elements may each include a support element affixed therewith.

In another embodiment, a method of implanting an expansible heart valve prosthesis in the heart of a patient is provided. This method includes delivering an expansible helical anchor in the form of multiple coils such that a portion of the expansible helical anchor is above the native heart valve and a portion is below the native heart valve. The expansible heart valve prosthesis is positioned within the multiple coils of the expansible helical anchor with the expansible heart valve prosthesis and the expansible helical anchor in unexpanded states. The expansible heart valve prosthesis in then expanded against the expansible helical anchor thereby securing the expansible heart valve prosthesis to the expansible helical anchor. By "expansible" it is meant that at least one coil of the anchor enlarges in diameter.

The method may further include moving a coil from a larger diameter to a smaller diameter as the heart valve prosthesis is expanded inside the multiple coils. At least two adjacent coils of the helical anchor may be spaced apart, and the method further comprises moving the at least two adjacent coils toward each other as the heart valve prosthesis is expanded inside the multiple coils. The helical anchor further may comprise a plurality of fasteners, and the method further comprises moving the fasteners from an undeployed state to a deployed state as the expansible heart valve prosthesis is expanded against the expansible helical anchor. A seal may be positioned between adjacent coils for preventing blood leakage through the helical anchor and past the heart valve prosthesis and the fasteners engage the seal in the deployed state. The fasteners may instead engage a portion of the anchor which is not a seal. Any other aspects of the methods or systems disclosed herein may also or alternatively be used in this method depending on the desired outcome.

Various additional advantages, methods, devices, systems and features will become more readily apparent to those of ordinary skill in the art upon review of the following detailed description of the illustrative embodiments taken in conjunction with the accompanying drawings.

BRIEF DESCRIPTION OF THE DRAWINGS

FIG. 7D-1 is a cross-sectional view of an implanted replacement heart valve within a helical anchor, similar to FIG. 7D but illustrating alternative configurations for the replacement heart valve and the anchor.

FIG. 9A is an elevational view of another embodiment of a helical anchor being expanded by a balloon catheter.

FIG. 9B is a view similar to FIG. 9A, but illustrating further expansion of the balloon catheter.

FIG. 9C is a view similar to FIG. 9B but illustrating even further expansion of the balloon catheter.

FIG. 9D is an enlarged cross-sectional view showing compression of the helical coils from FIG. 9C.

FIG. 10C-1 is an enlarged cross-sectional view showing engagement between the stent of the replacement heart valve and the helical anchor.

DETAILED DESCRIPTION OF THE ILLUSTRATIVE EMBODIMENTS

Figure 1A:
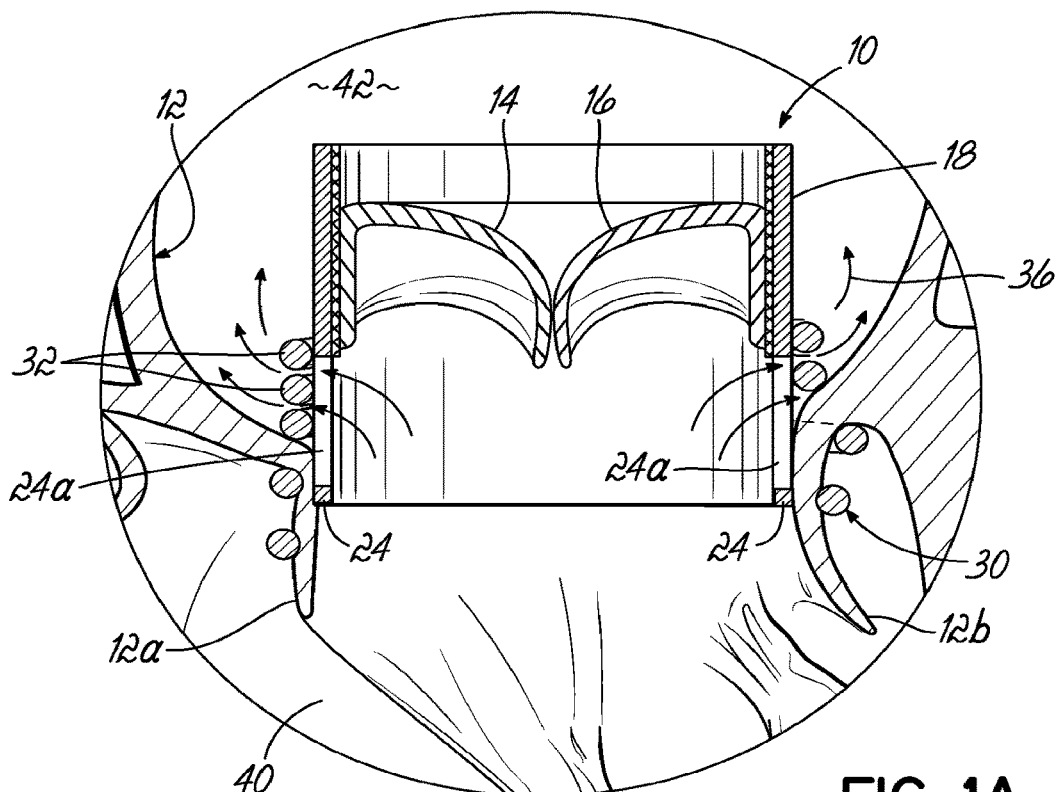
FIG. 1A is a schematic cross-sectional view illustrating a replacement heart valve implanted in a native valve position using a helical anchor.

It will be appreciated that like reference numerals are used to refer to generally like structure or features in each of the drawings. Differences between such elements will generally be described, as needed, but the same structure need not be described repeatedly for each figure as prior description may be referred to instead for purposes of clarity and conciseness. FIG. 1 schematically illustrates a typical replacement heart valve or prosthesis 10 that may be implanted in the position of a native heart valve, such as the mitral valve 12, using a catheter (not shown). A sealed condition is desired around the valve 10, i.e., between the periphery of the replacement valve 10 and the native biologic tissue, in order to prevent leakage of blood around the periphery of the replacement valve 10 as the leaflets 14, 16 of the replacement valve 10 open and close during systolic and diastolic phases of the heart. The portion of the replacement heart valve 10 intended to be positioned in contact with native tissue includes a fabric or polymeric covering 18 to prevent regurgitation of blood flow. In FIG. 1A, the fabric cover 18 is shown adjacent to the replacement valve leaflets 14, 16 within the stent mounted replacement valve 10. These replacement valve leaflets 14, 16 are typically formed from biologic material, such as from a cow or a pig, but may synthetic or other bioforms. Approximately half of this replacement valve 10 has no seal, i.e., it is more or less exposed stent 24 with openings 24a. This is because when the replacement valve 10 is placed in the aortic native position, the coronary arteries arise just above the aortic valve. If the seal 18 extended the entire length of the stent portion 24 of the replacement valve 10, the coronary artery could be blocked. In FIG. 1A, an unmodified aortic replacement valve 10 is shown implanted in a helical anchor 30 comprised of coils 32. Leakage of blood flow may occur as depicted schematically by the arrows 36, because there is a gap between the seal 18 on the stented valve 10 and the attachment to the patient's mitral valve 12. The leakage of blood flow may occur in any direction. Here, the arrows 36 depict the leak occurring from the ventricle 40 to the atrium 42 since the ventricular pressure is higher than the atrial pressure. An unmodified aortic valve 10 placed in the native mitral valve position will be prone to develop a leak. To avoid this problem, two major approaches may be taken. First, a seal may be added to the system, for example, the helical anchor 30 may have sealing features added. Second, the location where the stent mounted replacement heart valve 10 sits may be changed. In this regard, if the replacement heart valve 10 is positioned lower inside the ventricle 40, the seal 18 on the replacement heart valve 10 will be situated such that there is no leak. One drawback to seating the valve 10 lower inside the left ventricle 40 is that the replacement heart valve 10 may cause damage inside the left ventricle 40 or the valve 10 may obstruct ventricular contraction. The replacement heart valve 10 may damage the ventricular wall or block the outflow of blood from the ventricle 40 into the aorta. Rather than simply seating the replacement heart valve 10 more deeply or lower into the left ventricle 40, it may be useful to keep the position of the stent mounted replacement valve 10 more atrially positioned as it is depicted in FIG. 1A (i.e., positioned higher and extending into the atrium 42).

Figure 1B:
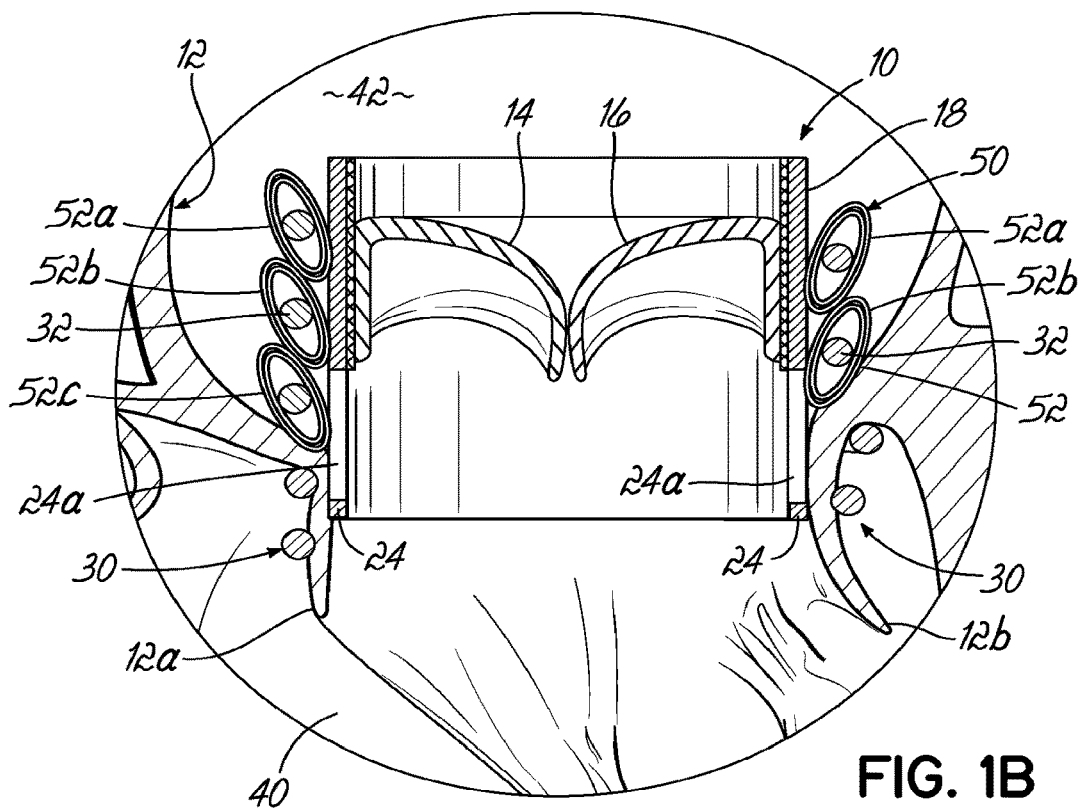
FIG. 1B is a schematic cross-sectional view similar to the FIG. 1A, but illustrating the use of seals in conjunction with the helical anchor.

FIG. 1B illustrates one embodiment of providing seal structure 50 at the upper portion of a replacement heart valve 10 to prevent blood flow leakage as discussed above and shown in FIG. 1A. In this regard, one or more seals 52 have been added to the helical anchor 30. Specifically, a fabric covered oval seal structure 52 is added to the helical anchor 30 to provide a seal. The seal 52 may be formed from fabric, or any other material that provides a sufficient seal and does not allow blood to flow through. The seal 52 extends down to the level of the attachment between the stent mounted replacement valve 10 and the native mitral leaflets 12a, 12b. The seal 52, in this illustrative embodiment is a continuous tube and comprises one or more seal elements or portions 52a, 52b, 52c in the form of overlapping segments of fabric or other sealing material. These segments 52a, 52b, 52c of sealing structure act as siding structure or shingles to seal the space between the coils 32 or turns of the helical anchor 30.

Figure 2A:
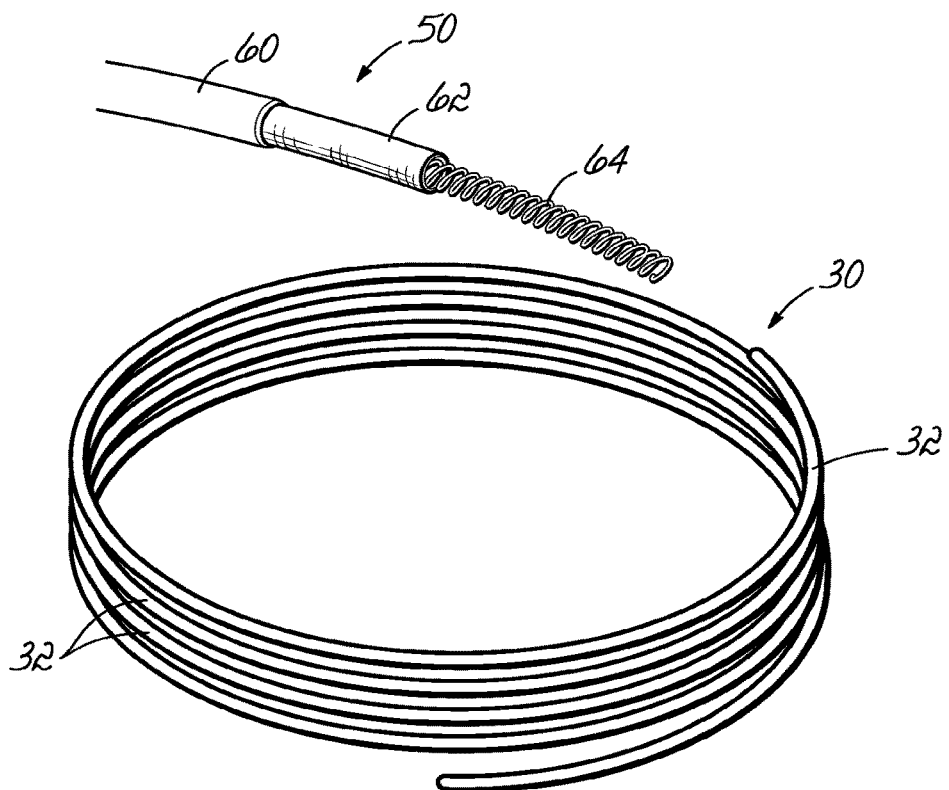
FIG. 2A is a perspective view illustrating one method of applying the seal structure to the helical anchor.
Figure 2B:
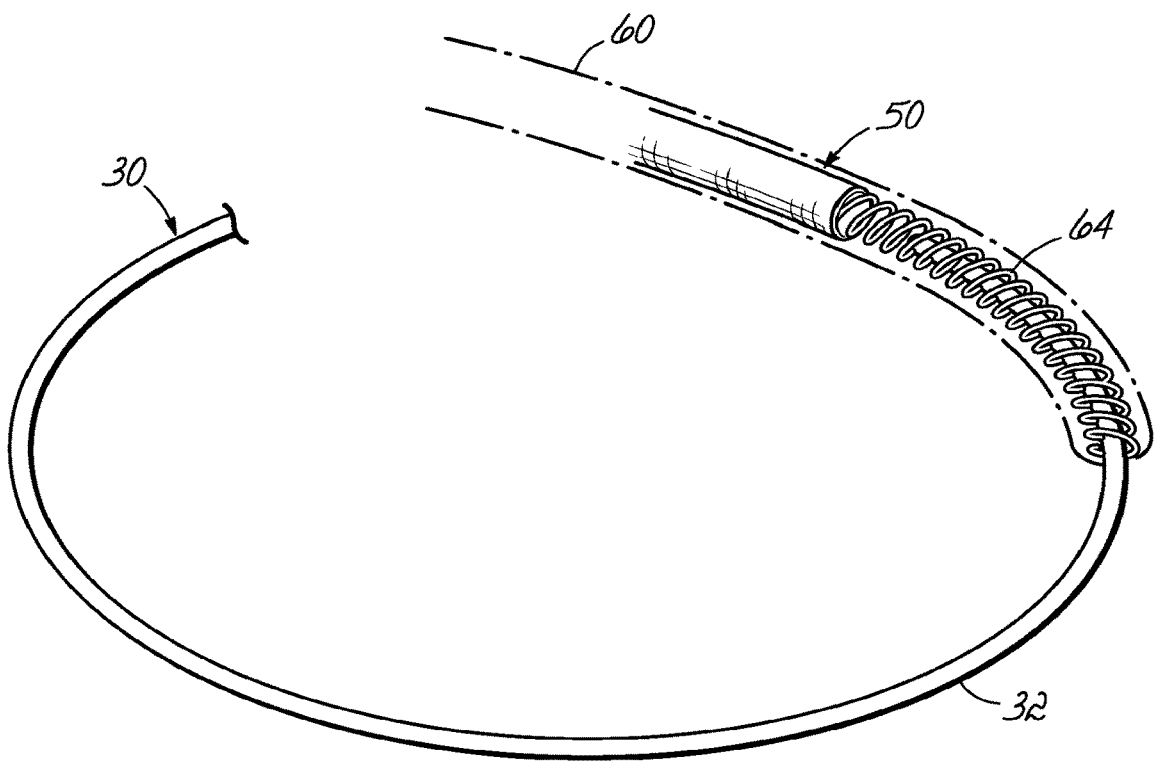
FIG. 2B is a perspective view illustrating a further step in the method illustrated in FIG. 2A.
Figure 2C:
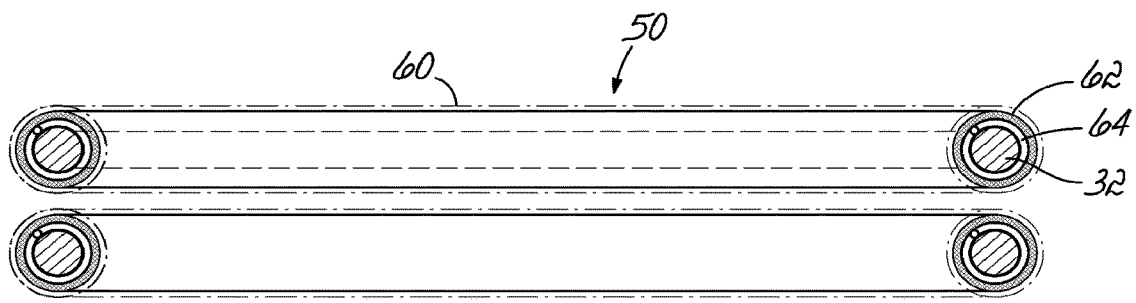
FIG. 2C is a cross-sectional view showing the helical anchor after application of the seal.

FIG. 2A illustrates one manner of applying the overlapping seal structure 50 such as shown in FIG. 1B or otherwise integrating the seal structure 50 on the helical anchor 30. In this regard, the seal structure 50 may be integrated with the helical anchor 30 for delivery purposes. The shingles or overlapping seal portions 52a-c (FIG. 1B) may be collapsed and extruded from a catheter 60. Alternatively, once the helical anchor 30 has been delivered to the native heart valve site, the fabric or other seal structure 50 may be delivered over the coils 32 of the anchor 30 from the same delivery catheter 60. Alternatively, the overlapping seal structure 50 may be added to the helical anchor 30 as the helical anchor 30 is being extruded or extended from the delivery catheter 60. FIG. 2A specifically illustrates a helical anchor 30 with a fabric or other seal structure 50 being fed over the helical coils 32 from a sheath or delivery catheter 60. The seal structure 50 may be generally circular in cross section or any other shape, such as a shape that is better configured for overlapping as generally shown in FIG. 1B above. FIG. 2B illustrates fabric 62 and an internal support coil 64 being added to the helical anchor 30 in a further portion or step of the procedure illustrated in FIG. 2A. FIG. 2C illustrates one embodiment of a completed assembly, shown in cross section, comprising the helical anchor 30 covered by the coil 64 and fabric 62 and delivered by a sheath or delivery catheter 60. The delivery sheath or catheter 60 may remain over the coil and fabric combination or it may be used to merely deliver these sealing elements 62, 64 over the helical anchor 30.

Figure 2D:
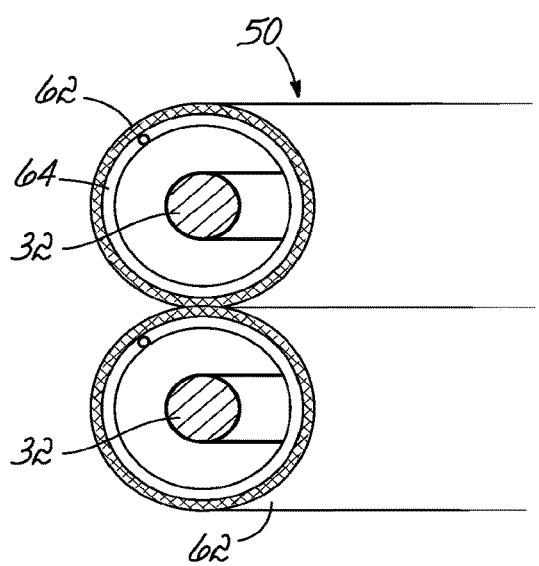
FIG. 2D is an enlarged cross-sectional view of the helical anchor having one form of seal applied.

FIG. 2D illustrates a cross sectional view of the sealing elements 62, 64 which, in this case, are circular in cross section. These sealing elements 62, 64, including, for example, a coil support and fabric combination, may be virtually any shape as long as they provide a seal when placed together. Sealing elements 62, 64 may not overlap in use but instead contact each other as shown to create a seal therebetween.

Figure 2E:
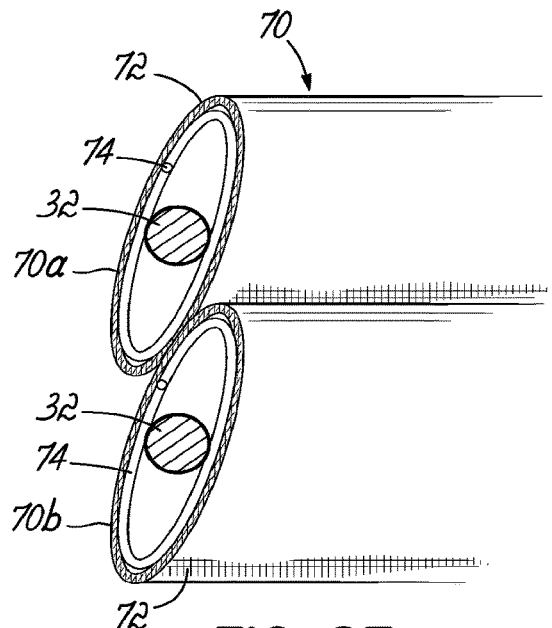
FIG. 2E is a cross-sectional view similar to FIG. 2D, but illustrating an alternative embodiment of the seal.

FIG. 2E shows an oblong or oval cross sectionally shaped seal structure 70 similar to the seal 50 shown in FIG. 1B in which segments 70a, 70b overlap each other to produce a secure and fluidtight seal. It is possible to have the oblong seal structure 70 compressed for delivery and then spring or bias open once the seal structure 70 is extruded from a delivery catheter or sheath. A coil 74 internally supporting fabric 72 may be made of Nitinol (superelastic) wire or spring steel wire so that it may be collapsed and then bias or spring into a predetermined shape as needed.

Figure 2F:
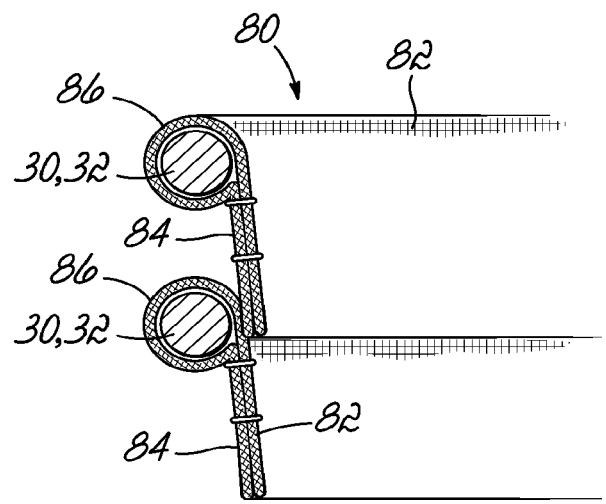
FIG. 2F is another enlarged cross-sectional view similar to FIG. 2E but illustrating another alternative embodiment for the seal.

FIG. 2F shows another alternative seal structure 80. In this case, a sealing fabric 82 or other material is wrapped around the helical anchor 30. The fabric is stitched together with suitable thread to form stiff, structural panels 84 extending from the connecting portion 86 that is affixed to a coil 32 of the helical anchor 30. The panels 84 again overlap, similar to a shingle effect, to provide a fluidtight seal. This configuration may be delivered in a similar manner to the previously described fabric covered coil designs above by passing the panel structure over the helical anchor 30 as shown.

Figure 3A:
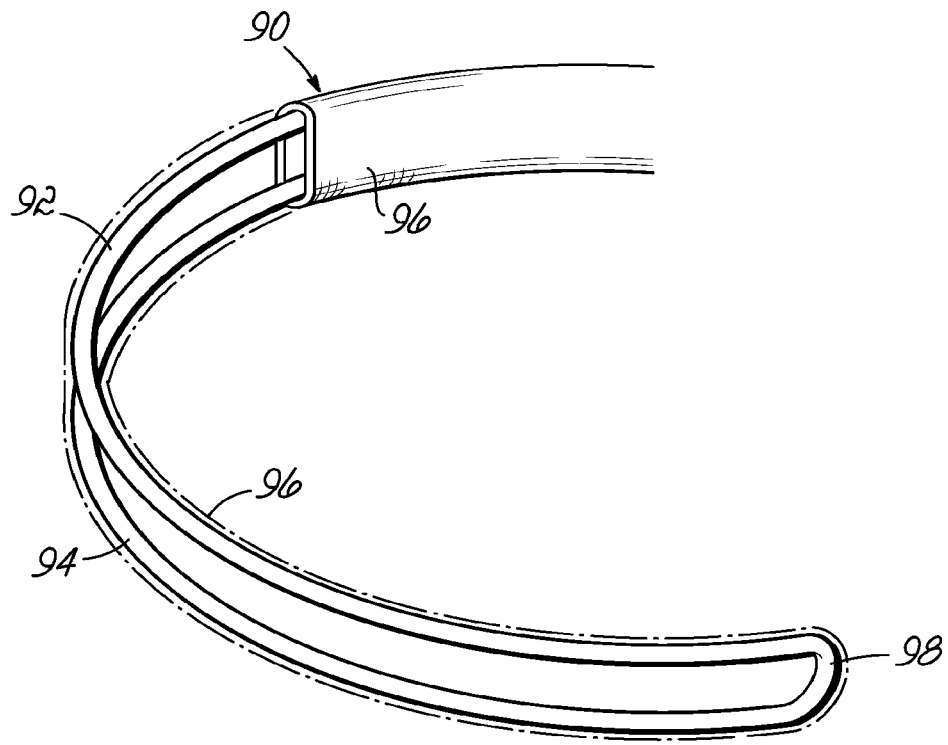
FIG. 3A is a schematic perspective view illustrating another alternative embodiment of the helical anchor and seal.

FIG. 3A illustrates another embodiment for providing a sealing structure. In order to provide further shape and support to a seal structure 90, there may be two or more "framing" segments 92, 94 inside a fabric covering 96 or other material seal. This will give a shape to the seal structure 90 and provide for more reliable overlap of the seal segments (only one shown in FIG. 3A). This may be achieved by using a double helix in which two wires 92, 94 run parallel to each other to form a helical shape. The two wires 92, 94 may be connected at their ends with a curved section 98 as shown in FIG. 3A. The fabric or other material sleeve or coating 96 may be passed over the double helix during or after delivery of this helical seal structure 90.

Figure 3B:
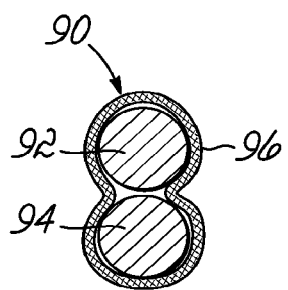
FIG. 3B is a cross-sectional view of the embodiment shown in FIG. 3A, with the helical adjacent coils compressed together for delivery.

FIG. 3B illustrates a cross sectional view of the seal structure 90 compressed with wires 92, 94 inside the outer fabric or other material 96. This can provide for easier delivery to the site of implantation.

Figure 3C:
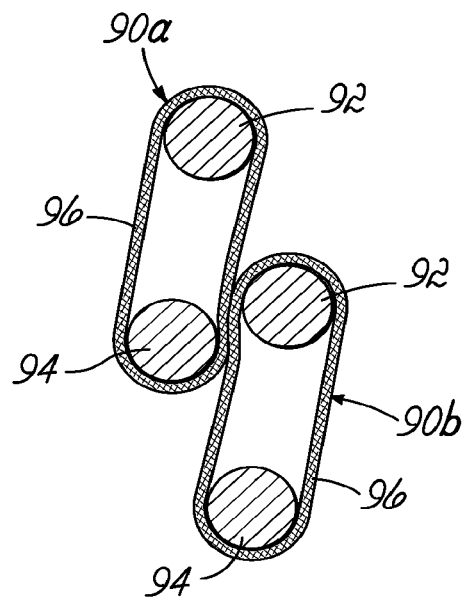
FIG. 3C is a cross-sectional view showing the helical anchor and seal expanded after delivery.

FIG. 3C illustrates the double helix seal 90 spread apart and overlapping after delivery. Two segments 90a, 90b of the helical seal 90 can expand as they are being delivered to form overlapping seal segments 90a, 90b similar to the "shingle" configuration discussed above. Here, two overlapping seal segments 90a, 90b are supported by two double helix frames 92, 94 positioned adjacent and overlapping to each other to produce an effective, fluidtight seal.

Figure 3D:
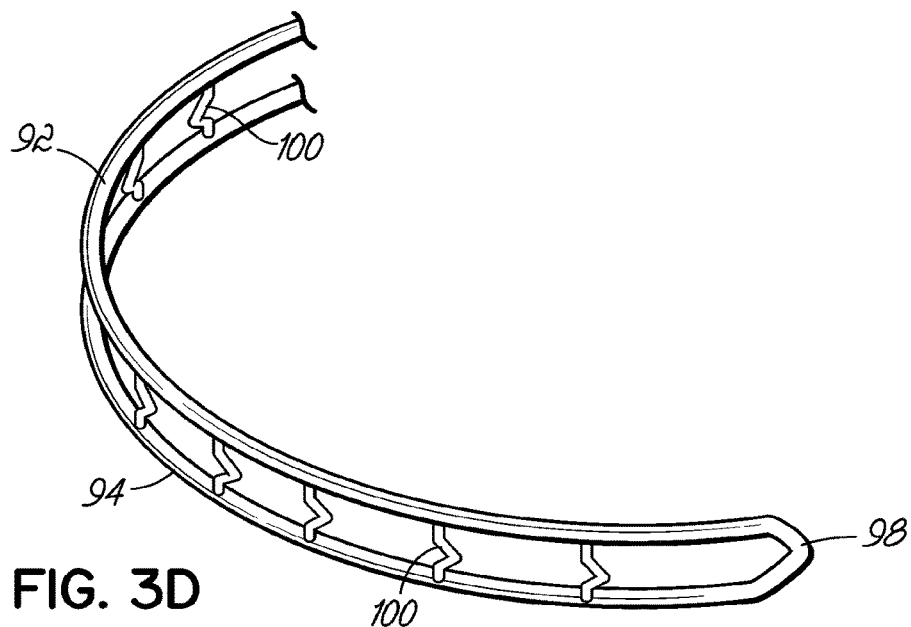
FIG. 3D is a partial perspective view illustrating another illustrative embodiment of the helical anchor.

FIG. 3D illustrates another alternative method for coupling frame segments 92, 94 of a seal and, specifically, biasing the frame segments 92, 94 apart. Interconnecting segments 100 between the two frame parts or wires 92, 94 can push the frame segments 92, 94 into a desired final shape. This double helix design may be made from multiple wire pieces or may be made from a single solid Nitinol or steel tube or wire, similar to stent manufacture techniques. The seal frame 92, 94 may also have a sinusoidal or generally back and forth configuration (not shown) to hold a shingle-type shape rather than two rails or wires inside of the outer seal material or fabric 96 (FIG. 3C).

Figure 3E:
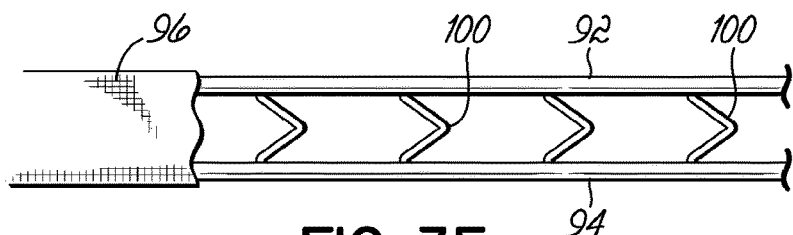
FIG. 3E is a schematic elevational view, partially fragmented, to show the application of a seal to the helical anchor structure of FIG. 3D.

FIG. 3E details how the outer seal material or fabric 96 may be placed over the expanded frame 92, 94. The seal material 96 may be preattached to the double helix frame 92, 94 and the two may be delivered together. Alternatively, the seal material 96 may be delivered onto the double helix frame 92, 94 after the double helix frame 92, 94 is already in place at the implantation site, such as the site of a native mitral valve. In the unexpanded state, the double helix 92, 94 may be extruded through a catheter as previously described.

Figure 3F:
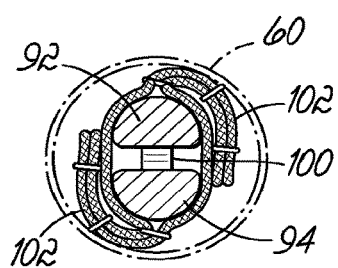
FIG. 3F is an enlarged cross-sectional view illustrating another embodiment of a helical coil structure with a seal.
Figure 3G:
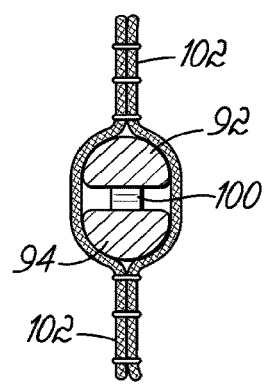
FIG. 3G is a cross-sectional view similar to FIG. 3F, but illustrating the structure after delivery and unfolding of the seal.
Figure 3H:
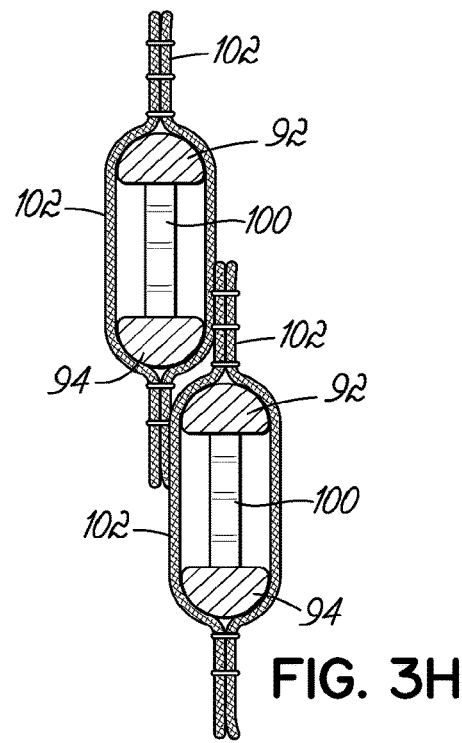
FIG. 3H is a cross-sectional view similar to FIG. 3G but illustrating multiple parts of the helical anchor structure and associated seal expanded after delivery.

FIGS. 3F, 3G and 3H generally show the progression of delivery and implantation of the seal 90. In these figures, the seal material or fabric 96 extends beyond the frame 92, 94 to form flaps or panels 102 of seal material. These flaps or panels 102 may be stiffened and reinforced with heavy suture, or the material may be soaked or coated in a stiffening agent. This may be useful to ensure a fluidtight seal. In FIG. 3F, the internal wire frame 92, 94 is collapsed and the fabric cover 96, 102 is folded within a delivery sheath 60 for delivery. In FIG. 3G the frame 92, 94 has been delivered and the segments or flaps 102 of seal material 96 that extend beyond the frame 92, 94 have unfolded. FIG. 3H illustrates the frame parts 92, 94 expanded, in a manner similar to a stent. This provides a solid and secure seal. The cross members or biasing members 100 that were collapsed inside the double helix frame 92, 94 are now biased outward and lengthened or straightened. These cross members 100 may be made of Nitinol or other spring material and expand the frame 92, 94 with a spring force as the frame 92, 94 is delivered from a catheter or sheath 60. Alternatively, there may be another mechanism or manner for activating and expanding the frame 92, 94 as needed during the implantation procedure.

Figure 4A:
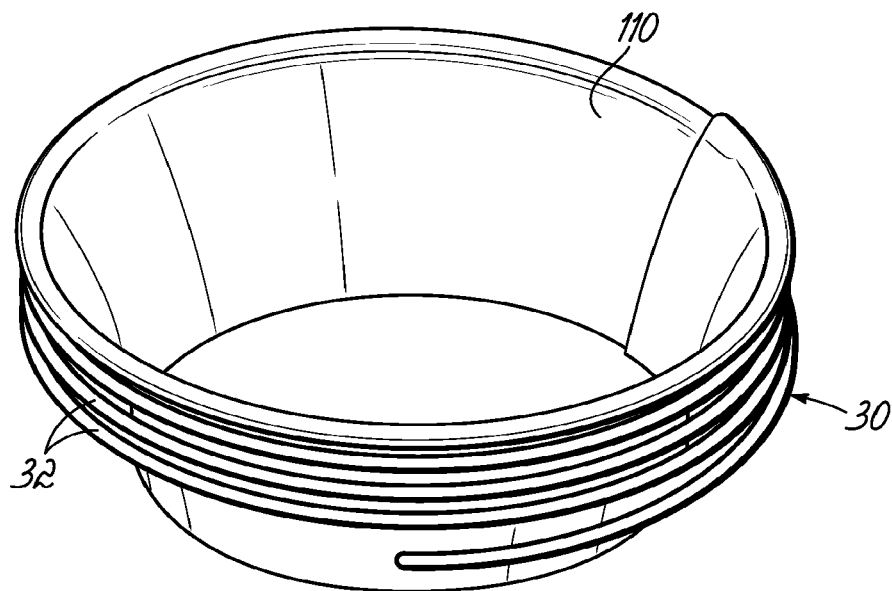
FIG. 4A is a perspective view illustrating a helical anchor in combination with another alternative embodiment of a seal.

FIG. 4A illustrates another embodiment for adding sealing features to a helical anchor 30. Here, a fabric windsock-type shape or panel/membrane structure 110 has been mounted to an upper turn or coil 32 of the helical anchor 30. This panel 110 unfolds or extends within the helical anchor 30 to provide a sealing membrane. The fabric or other seal material may be sewed or permanently fastened to the helical anchor 30. Alternatively, this seal panel 110 may be delivered onto the helical anchor 30 after the helical anchor 30 is placed at the site of implantation within a native heart valve. The seal material 110 may be attached on any portion of the helical anchor 30 at any level of the anchor 30. In FIG. 4A, the seal panel 110 is attached to the uppermost coil 32 of the helical anchor 30 such that the panel 110 can then expand to the full length of the helical anchor 30 and provide a full length, fluidtight seal.

Figure 4B:
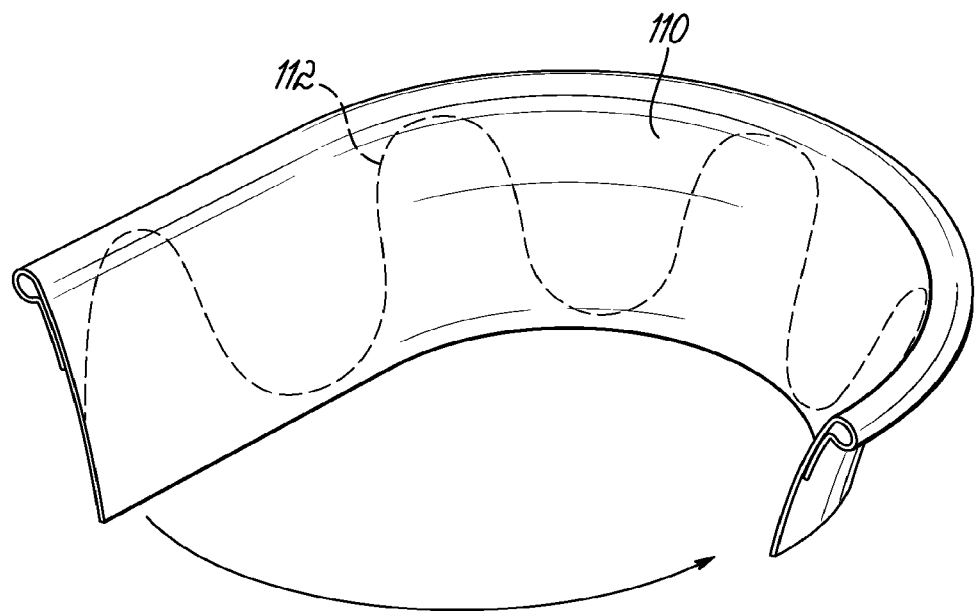
FIG. 4B is a perspective view of the seal illustrating an alternative embodiment which adds support structure to the seal.

FIG. 4B illustrates the seal panel 110 opened and an internal support structure 112, in the form of a wire or sinusoidal-type support element inside or within layers of the seal material. This support structure 112 for the seal 110 may be made of, for example, Nitinol or steel. The support 112 may be sewn into the fabric or otherwise secured to the seal material. The fabric may, for example, contain a channel for the support 112 and the support 112 could be pushed into the channel, expanding the seal material 110 as needed. If the support 112 is made from Nitinol or superelastic material, and imbedded inside the fabric or seal material 110, it may straighten and fold up the fabric or other seal material inside a delivery catheter or sheath. While being delivered, the Nitinol or superelastic support would return to its initial zigzag or sinusoidal shape, expanding the fabric as it is released and extruded from the delivery sheath or catheter.

Figure 4C:
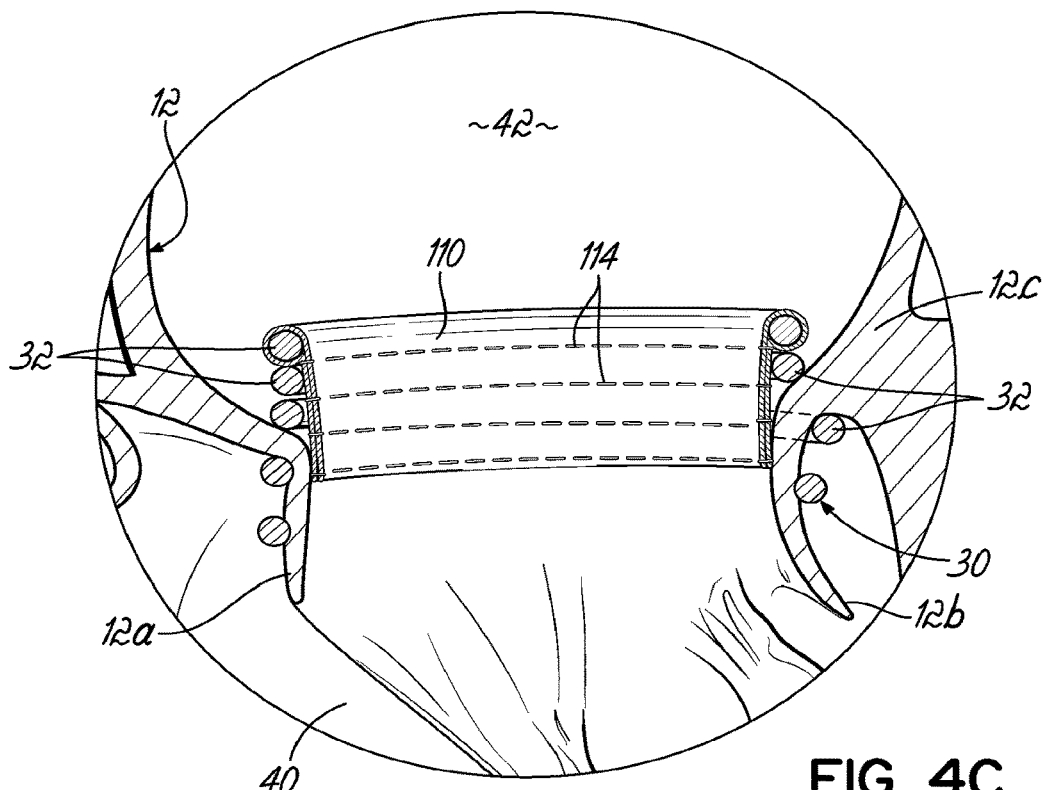
FIG. 4C is a schematic cross-sectional view illustrating the embodiment of FIG. 4A implanted in a native heart valve position.

FIG. 4C is a cross sectional view illustrating a helical anchor 30 and fabric seal panel 110, such as shown in FIG. 4A delivered and implanted at a native valve site, such as within the mitral valve 12 of a patient. The seal panel 110 is annular in shape and generally follows the interior of the helical anchor 30. As shown here, the fabric panel 110 is stitched to the upper turn or coil 32 of the helical anchor 30 and the fabric is folded on itself and stitched together as shown. Stitching 114 can also provide structural support to help the fabric shape itself correctly. The stitching may be made of steel wire or Nitinol wire that may assist in providing shape stability to the membrane or panel structure 110. The stitching 114 may also be suture or thread. The heavier the stitching material, the more support it will provide for the fabric. Here, the stitching is in horizontal lines, however, it may instead be other configurations such as vertical, zigzag, or any other suitable configuration.

Figure 4D:
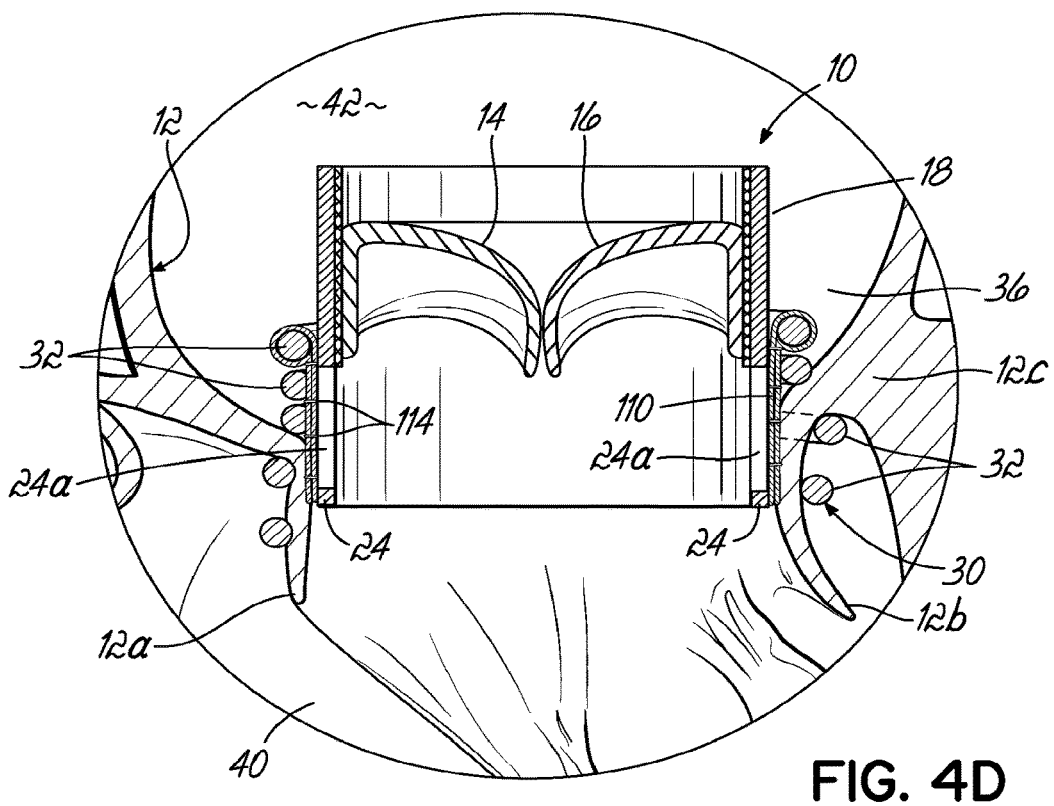
FIG. 4D is a schematic cross-sectional view illustrating a replacement heart valve implanted within the helical anchor and seal structure of FIG. 4C.

FIG. 4D illustrates a stent mounted heart valve 10 expanded within the helical anchor 30 and seal structure 110 of FIG. 4C. The seal 110 prevents any leakage of blood around the valve 10 and covers any areas of the stent portion 24 of the valve 10 that are not already covered and sealed. The seal 110 allows the replacement heart valve 10 to be seated higher toward the atrium 42, thereby reducing the risk of left ventricle injury or left ventricle blood outflow obstruction.

Figure 5A:
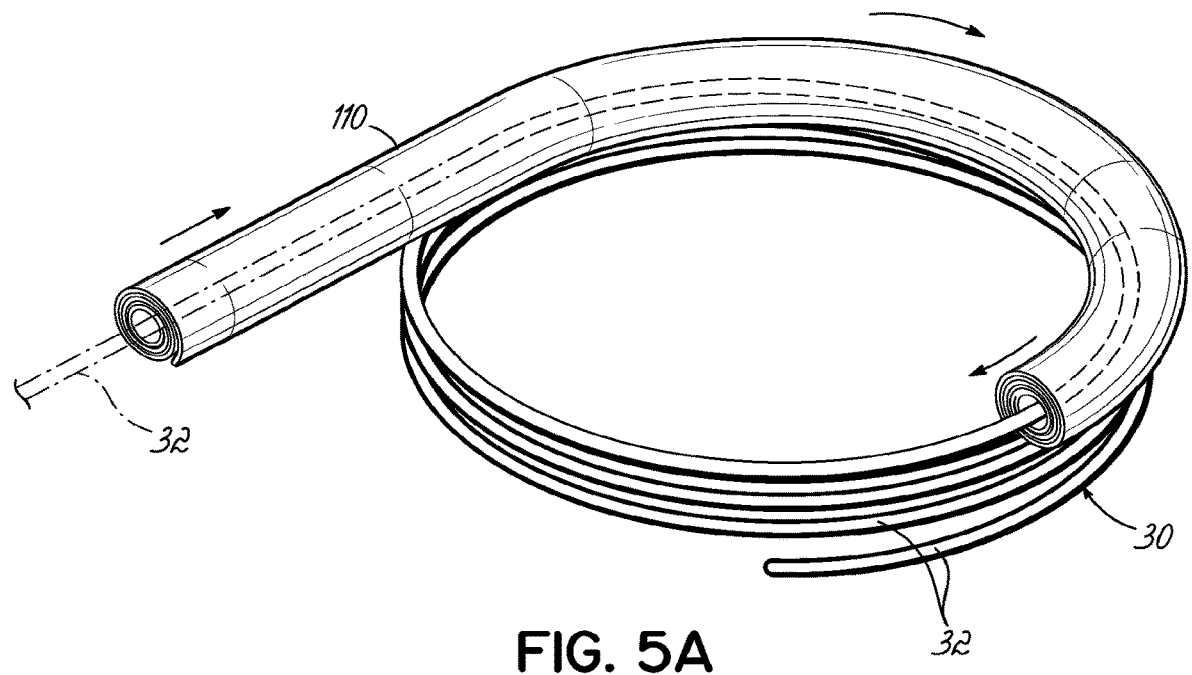
FIG. 5A is a perspective view of a helical anchor with a membrane or panel seal being applied.
Figure 5B:
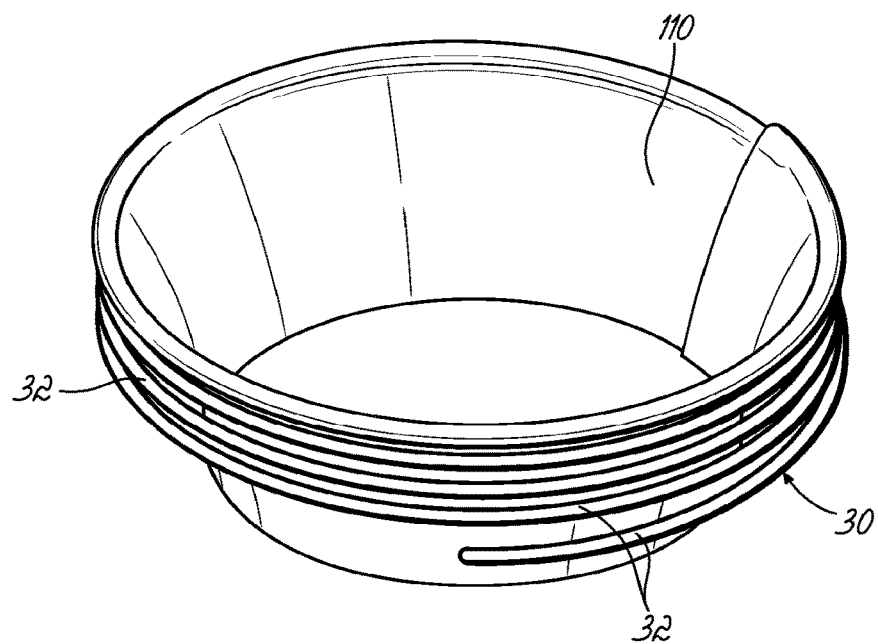
FIG. 5B is a perspective view of the helical anchor with the membrane or panel seal of FIG. 5A deployed or unfolded.

FIG. 5A illustrates a helical anchor 30 with an attached membrane or panel seal 110 being delivered onto the coils 32 of the helical anchor 30. It should also be noted that the membrane or panel seal 110 can also improve the attachment of the replacement heart valve 10. In this regard, a bare helical anchor 30, particularly one made of metal that attaches to a metal stent will result in metal surfaces contacting each other. As the heart beats and pressure rises with each contraction, e.g., about 100,000 times per day, there is a risk of slippage between the metal surfaces and potential valve dislodgement. Therefore, the addition of a membrane, panel 110 or other seal structure can reduce the tendency for the valves to slip and even fail. The membrane or seal panel 110 may be smooth or have various degrees of texture or roughness to help maintain fixation of the replacement heart valve 10. Textured or roughened surfaces will increase friction and therefore reduce slippage. Also, the fabric or other seal material 110 may be forced inside the openings or cells of the stent portion 24 of the replacement heart valve 10 thereby improving or creating a locking effect and anchoring the stent mounted replacement valve 10 to the helical anchor 30, including the seal material 110. In FIG. 5A, the membrane or panel seal 110 is attached to the helical anchor 30 and as previously described, the membrane or panel seal 110 may be attached prior to implantation within the patient or added at any point during the implantation procedure. It may be advantageous to add the membrane or panel seal 110 after the helical anchor 30 is placed at the implantation site in order to reduce complication during delivery of the helical anchor 30. FIG. 5B illustrates the membrane seal or panel seal 110 unfolded or expanded within the helical anchor 30. As previously described, the membrane or panel seal 110 is attached to the uppermost turn 32 of the helical anchor 30, however, it may be attached anywhere along the helical anchor 30. The membrane or panel seal 110 may be continuous or intermittent, and may be comprised of overlapping panel portions similar to a shingle effect. Although the membrane or panel seal 110 makes a complete annulus as shown in FIG. 5B within the helical anchor 30, it may instead be formed as less than a complete annulus.

Figure 5C:
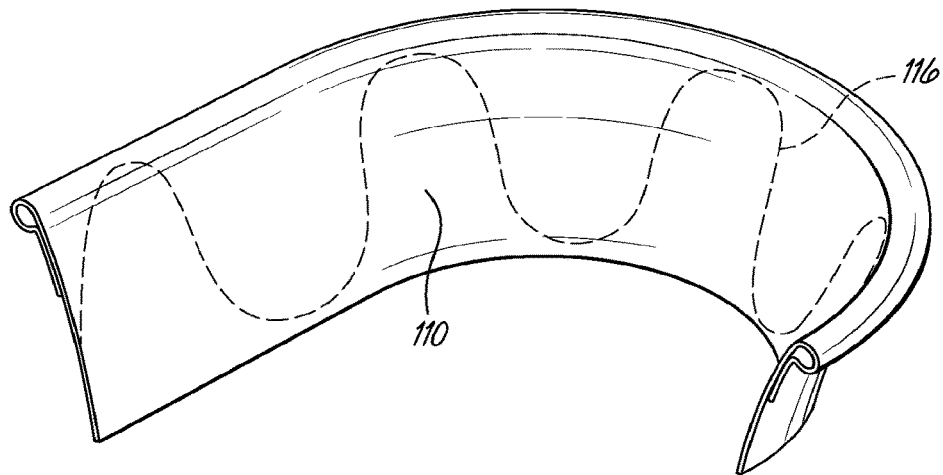
FIG. 5C illustrates a perspective view of the membrane or panel seal with an internal support structure.

FIG. 5C is similar to FIG. 4B described above and simply illustrates that in this embodiment, the delivered and deployed membrane seal 110 may also include a similar internal support 116. It is also possible that the membrane or panel seal 110 is intrinsically stiff and springs open without internal support structure of any sort. Many other ways to open or deploy the membrane or panel seal 110 may used instead. For example, the panel seal 110 may contain pillars or other supports (not shown) that are collapsed for delivery but that allow the membrane or panel 110 to be biased open once the membrane or panel 110 is delivered from a suitable catheter or sheath. These pillars or other supports may, for example, be formed from shape memory or superelastic material, or other suitable spring biased material.

Figure 5D:
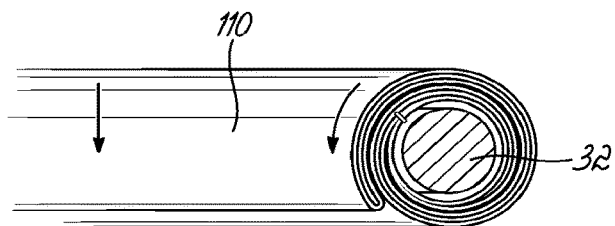
FIG. 5D is an enlarged cross-sectional view of the helical coil and undeployed membrane seal.

FIG. 5D illustrates the panel seal 110 unwinding or being deployed. The panel seal 110, in this illustrative embodiment, is formed of two layers with a support 116 between these two layers. The support 116, as described above, is suitably secured between the layers of the panel seal 110. Although shown as a sinusoidal configuration, the support 116 may be of any desired and suitable configuration, or may be comprised of separate support structures such as generally circular or oval support structures (not shown). Other useful structures in this regard may include any of those shown and described in U.S. Provisional Patent Application Ser. No. 61/864,860, filed on Aug. 12, 2013, the disclosure of which is hereby fully incorporated by reference herein. Finally, drawstrings (not shown) may be added to the end of the membrane seal 110 or to any part or parts of the membrane seal 110 that may be used to pull the membrane seal 110 open and unfold it or otherwise deploy it.

Figure 5E:
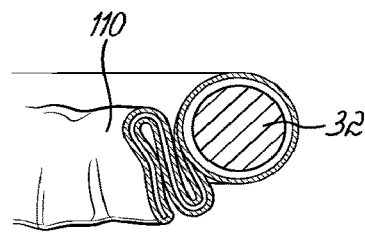
FIG. 5E is a cross-sectional view similar to FIG. 5D but illustrating a membrane seal which has been collapsed or folded rather than wound around a coil of the helix.

FIG. 5E illustrates a membrane or panel seal 100 which has been collapsed or folded onto itself rather than wound around the coil 32 of the helical anchor 30. A collapsed membrane seal 110 such as this may be more practical. The membrane or panel seal 110 can be opened with the support structure 116 normally biased to a deployed state as shown previously, or it may be deployed by containing structural support elements 116, such as shape memory support elements. As also previously discussed, drawstrings (not shown) might be added for deployment purposes.

Figure 5F:
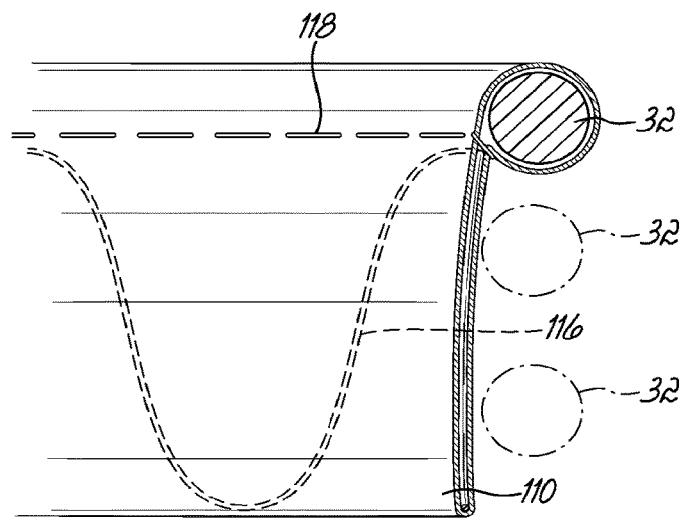
FIG. 5F is a perspective view of a portion of the coil and membrane seal illustrating further details including the internal support structure and a suture line.

FIG. 5F illustrates a cross sectional, enlarged view of the helical anchor 30 with the seal membrane 110 or panel extending adjacent to coils 32 of the helical anchor 30. The panel seal 110 includes a suture line 118 that keeps the seal 110 in place within the helical anchor 30, shown as a dotted line. This need not be a suture, instead, the securement may be provided by any suitable fasteners, glue, or other elements that maintain the membrane or panel seal 110 in position. In addition, the panel seal 110 may be glued or attached to the helical anchor 30 and this would eliminate the need for sutures or separate fasteners. As described previously, the panel seal 110 may be fabric or any other suitable biocompatible material. For example, the seal material in this and any other embodiment may be Dacron or Goretex, or may be biologic material from an animal or human. Other examples of seal material include engineered biomaterials or any combination of biologic and/or synthetic materials. The panel seal 110, in this embodiment, is opened with a spring biased support wire 116 as generally described above, but may be opened in any suitable manner during or after deployment and implantation of the helical anchor 30.

Figure 5G:
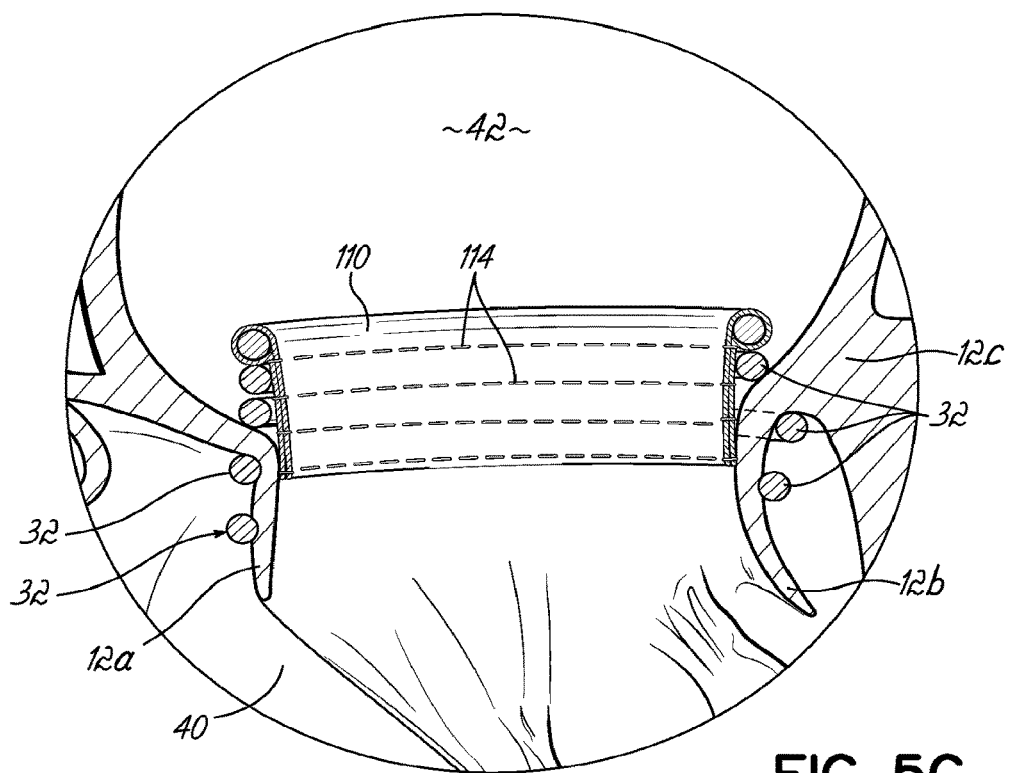
FIG. 5G is a cross-sectional view illustrating the helical coil and membrane seal implanted at a native heart valve site.
Figure 5H:
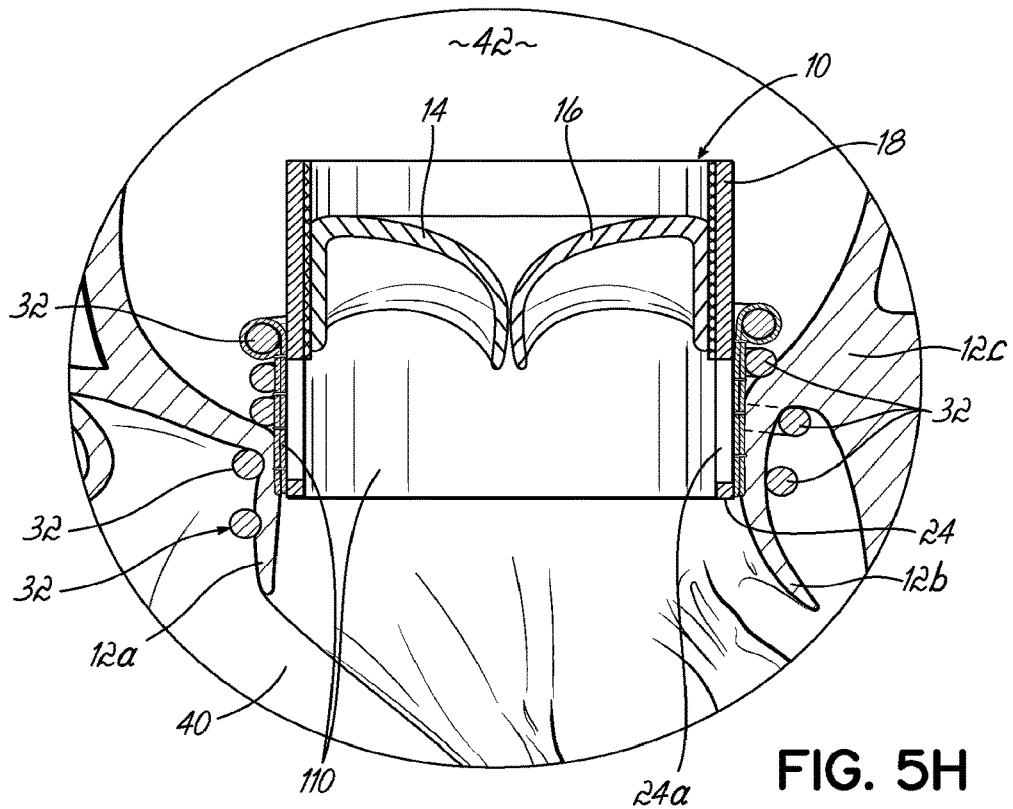
FIG. 5H is a cross-sectional view similar to FIG. 5G, but further illustrating a replacement or prosthetic heart valve implanted within the helical coil and membrane seal.

FIG. 5G illustrates the helical anchor 30 and panel seal 110 combination implanted at the site of a native mitral valve 12 of a patient. FIG. 5H illustrates a replacement heart valve 10, and specifically a stent mounted replacement heart valve 10 secured within the helical anchor 30 and panel seal 110 combination. These figures are described above with regard to FIGS. 4C and 4D. Thus, it will be appreciated that the panel seal structure 110 and helical anchor 30, regardless of deployment and delivery techniques, provide fluidtight sealing as previously described. It will be appreciated that additional features may be used to help deploy the panel seal or membrane 110 open as shown in FIGS. 5G and 5H. A foam layer (not shown) may also be positioned at any desired location, for example, to aid in sealing and/or valve retention. The membrane or panel seal 110 may extend the full length of the helical anchor 30 or only a portion of the length. In these figures, FIG. 5G illustrates the membrane or panel 110 extending only part of the length while FIG. 5H illustrates the panel or membrane 110 extending almost the entire length of the valve 10. As shown in FIG. 5H, the replacement heart valve 10 is positioned within the native mitral valve 12 such that much of the replacement heart valve 10 sits within the atrium. It will be appreciated that the replacement heart valve 10 may be positioned anywhere along the helical anchor 30. The helical anchor 30 may contain the entire prosthetic or replacement heart valve 10 or the replacement heart valve 10 may project at either end of the helical anchor 30 or from both ends of the helical anchor 30. The number of coils or turns 32 of the helical anchor 30 may also be varied. The key arrangement is to prevent as much leakage as possible, and maintain the replacement heart valve 10 securely in position after implantation.

In FIG. 5H one coil 32 of the anchor 30 extends beyond the stented prosthetic valve 10 inside the left ventricle 40. This may serve a number of functions. The end of the stent valve 10 is sharp and may damage structures inside the left ventricle 40. By leaving a turn 32 of the anchor 30 beyond the end of the valve 10, it may be possible to protect the structures inside the heart from contacting the sharp end of the valve 10. The lowest turn 32 of the anchor 30 may act as a "bumper" that is smooth and prevents injury to structures inside the ventricle 40. A smooth metallic (such as Nitinol) anchor coil 32 may be very well tolerated and prevent wear and abrasion inside the left ventricle 40.

The lowest turn or coil 32 of the anchor 30 may also wrap native mitral valve leaflet tissue around the end of the valve 10. This may also shield the sharp end of the prosthetic valve 10 from structures inside the heart.

The lowest turn or coil 32 of the helical anchor 30 may also provide tension on chordal structures. The function of the left ventricle 40 is improved and the shape of the left ventricle 40 can be optimized by placing tension on chordal structures. In FIG. 5H, the lowest coil 32 pulls the chordae toward the center of the ventricle 40 and shapes the left ventricle 40 optimally for contraction. It may be useful to have multiple coils 32 of the anchor 30 extending inside the left ventricle 40 beyond the anchor 30. These coils 32 could pull the chordae inward over a longer distance inside the heart. For example, if a patient had a very large left ventricle 40, it may be desirable to improve his left ventricular function by having a helical extension well beyond the valve 10. This would tighten the chordae and reshape the left ventricle 40. The coils 32 of the anchor 30 could also be heavier/thicker diameter to assist in reshaping the heart. The diameter of the coils 32 could also be varied to optimize the left ventricle shape change.

The concept of reshaping the left ventricle 40 with the anchor 30 does not need to apply to just mitral valve replacement. The helical anchors 30 shown in these descriptions can also be used for mitral valve repair. Extensions of the helix coils 32 inside the left ventricle 40 can also re-shape the left ventricle 40 even when a replacement prosthetic valve 10 is not used. As described previously, various numbers of coils 32, diameter of coils 32, thickness of materials, etc. could be used to achieve an optimal result.

It is also useful to use the helical anchor 30 to repair a native heart valve 12 and reshape the left ventricle 40 and leave open the possibility to add a prosthetic replacement valve 10 later if the repair fails over time. After surgical valve repair, this is not uncommon. An anchor 30 that serves as a repair device with or without left ventricular reshaping with coils 32 that extend into the left ventricle 40 may be useful as an anchor 30 if a prosthetic valve replacement is needed later.

Figure 6A:
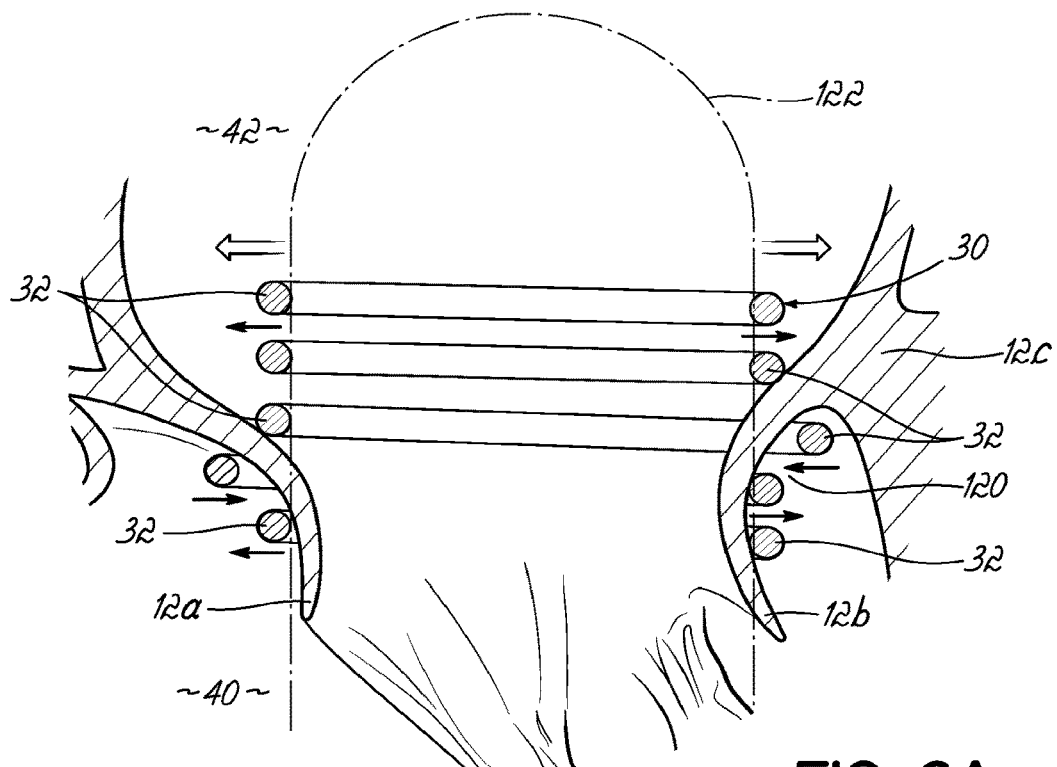
FIG. 6A is a cross-sectional view illustrating a helical coil implanted and at a native heart valve site being expanded by a balloon.

FIG. 6A illustrates a helical anchor 30 implanted at the native mitral valve position. In general, it will be important to seat the helical anchor 30 close to the under surface of the native mitral valve 12. If the diameter of the coils 32 or turns under the mitral valve 12 is relatively small, the helical anchor 30 is forced to slip down into the left ventricle 40. The helical anchor 30 attachment to the native valve 12 will be away from the annulus 12c and once the heart starts beating, the helical anchor 30 will be sitting inside the left ventricle 40 and, when there is mitral valve tissue between the helical anchor 30 and the mitral valve annulus 12c, the helical anchor 30 is not firmly attached in the annular region of the mitral valve 12, but rather to the leaflets 12a, 12b lower in the left ventricle 40, and this is not desirable. In FIG. 6A, a relatively large diameter turn or coil 32 of the helical anchor 30 is positioned just under the mitral valve leaflets 12a, 12b. This position is directly adjacent to the native mitral valve annulus 12c. Relatively smaller diameter coils 32 are positioned lower in the left ventricle 40. It may be useful to have a gap 120 between the relative larger coil 32 that is positioned under the valve leaflets 12a, 12b at the valve annulus 12c and the relatively smaller coil 32 positioned farther into the left ventricle 40. This will prevent the entire helical anchor 30 from being pulled down farther into the left ventricle 40 after implantation. Relatively smaller diameter coils 32 of the helical anchor 30 are positioned above the mitral valve 12, i.e., above the mitral valve native leaflets 12a, 12b. For illustrative purposes, a balloon 122 is shown for purposes of expanding the smaller diameter coils 32. This causes the larger diameter coil portions 32 to move relatively inward in a radial direction thereby tightening all of the coils 32 along a more similar diameter and tightening the connection between the helical anchor 30 and the native mitral valve tissue. Most importantly, the coil or turn 32 under the native mitral valve leaflets 12a 12b tends to grip against the underside of the mitral annulus 12c and pull the annulus radially inward, reducing the diameter of the native mitral annulus 12c. Annular reduction in this manner is important to improve left ventricular function when the heart is enlarged. Annular diameter reduction of a native mitral valve 12 is also important during mitral valve repair. The smaller diameter annulus adds to the improvement in left ventricular function. The concept of annular reduction using a sliding helical anchor 30 to control the leaflets 12a, 12b and pull the native mitral leaflets 12a, 12b and annulus 12c radially inward is specifically useful in mitral valve repair.

The concepts, methods and devices for improving left ventricular function in mitral valve prosthetic replacement, i.e., replacements that reduce the annulus diameter and tension chordae and reshape the left ventricle 40, will be invoked herein demonstrating mitral repair devices, concepts and methods. A smooth turn or coil 32 of the helical anchor 30 under the native mitral annulus 12 will have less tendency to grip against the mitral valve tissue and reduce the mitral valve annulus diameter. It may be useful to increase the "grip" of the turn or coil 32 under the annulus 12c for this reason. This may be accomplished in many ways including roughening the surface of the coil 32 such as by texturing the metal or by adding a high friction coating or fabric. The coating, fabric or other high friction material may be fixed to the helical anchor 30 or it may slide along the helical anchor 30. The high friction portion of the helical anchor 30 may be continuous or discontinuous.

Figure 6B:
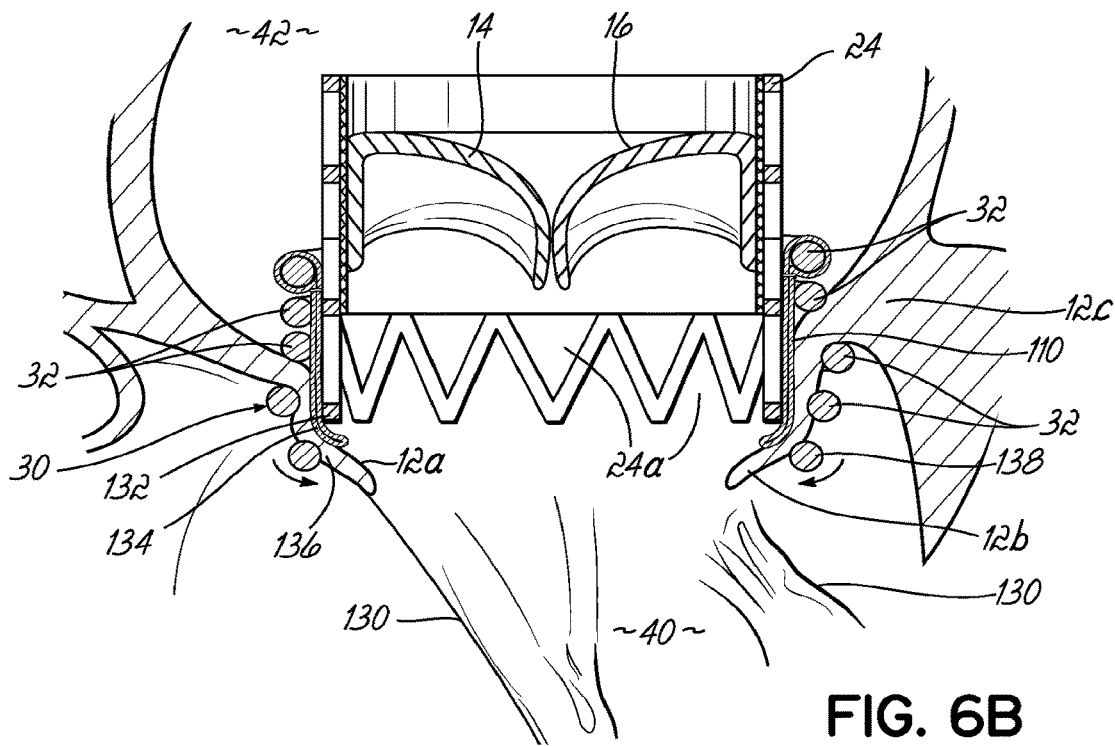
FIG. 6B is a cross-sectional view illustrating a stented, replacement or prosthetic heart valve implanted within a helical coil and membrane seal structure.

FIG. 6B illustrates the final position of the prosthetic replacement heart valve 10 inside the helical anchor 30 and its relation to the native mitral valve 12 and left ventricle structures. The left ventricle chordate 130 have been tensioned and, therefore, the left ventricle 40 has been appropriately reshaped. The sharp end 132 of the prosthetic replacement heart valve 10 has been covered by seal material 134, native valve tissue 136 and a "bumper" 138 of a lowest turn or coil 32 of the helical anchor 30. This provides multiple types of protection from injury inside the left ventricle 40 due to the sharp end of the stented prosthetic valve 10. Also note that the stented prosthetic heart valve 10 is positioned higher toward the atrium 42, and away from the structure in the left ventricle 40. This provides further protection from injury to the left ventricle 40 by the replacement heart valve 10. The fabric membrane seal, or other type of panel seal 110, may extend for any length. In this illustration it extends beyond the replacement heart valve 10. The fabric or other seal material may also extend beyond the end of the helical anchor 30 within the left ventricle 40. The fabric or other seal material 110 should cover the end of the replacement heart valve 10 until there is a seal at the level of the mitral valve 12. There is no need for a seal if the prosthetic replacement valve 10 has an attached seal or a seal is otherwise attached to the prosthetic replacement valve 10. In this case, useful features disclosed relate mainly to the attachment of the replacement valve 10 to the helical anchor 30 and the ability of the helical anchor 30 to reshape the left ventricle 40.

Figure 7A:
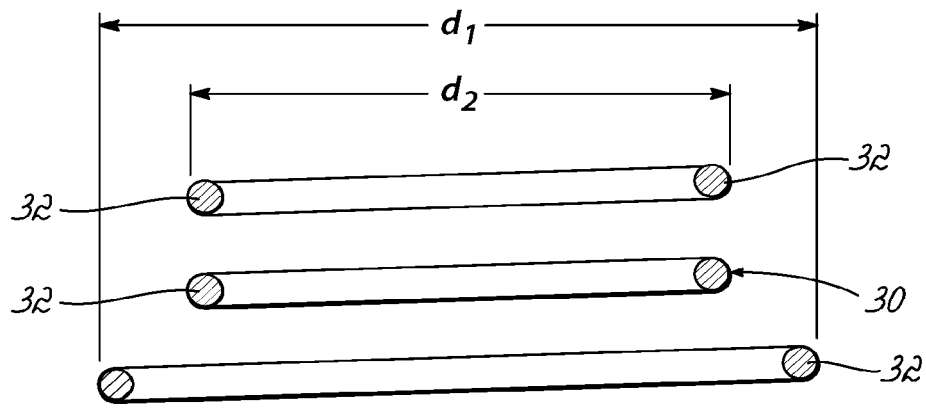
FIG. 7A is a cross-sectional view schematically illustrating a helical anchor having approximately two turns or coils having a first diameter and another coil having a second, larger diameter.
Figure 7B:
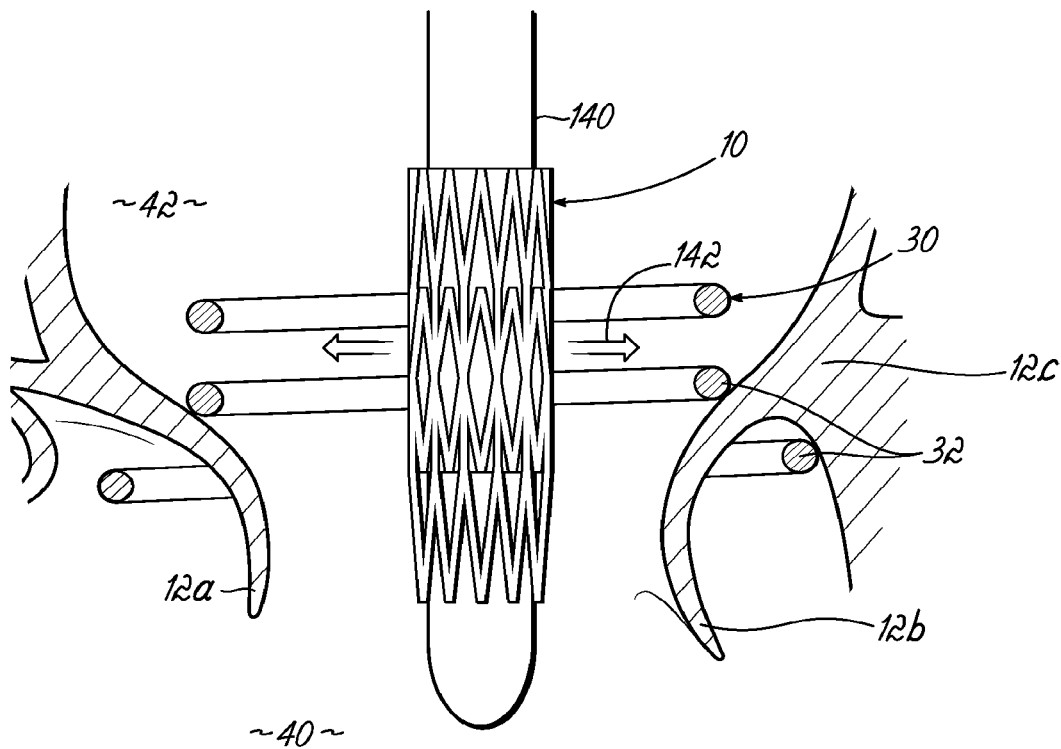
FIG. 7B illustrates an initial step during implantation of the helical anchor shown in FIG. 7A at a native heart valve site with a stent mounted replacement heart valve ready for implantation within the helical anchor.

FIGS. 7A-7D illustrates devices, methods and procedures relating to the interaction of the helical anchor 30, helical anchor design features and the stent mounted replacement heart valve 10 delivered or mounted on a balloon 140. Various catheters may be manipulated to take advantage of a design of the helical anchor 30 to improve valve implantation. For example, the stent mounted replacement valve 10 may be partially deployed and the helical anchor 30 manipulated with the stent mounted replacement valve 10 in a partially deployed state before the final deployment position is reached. FIG. 6A illustrates the helical anchor 30 with three coils or turns 32. The top two coils 32 have a relatively smaller dimension $d_2$ while the lowest turn or coil 32 has a relatively larger dimension or diameter $d_1$. FIG. 7B illustrates a stent mounted replacement valve 10 with a balloon 140 inside to deploy the valve 10 once the valve 10 has been positioned inside the helical anchor 30. The helical anchor 30 is placed with two of the coils or turns 32 positioned above the native mitral valve 12 and one coil or turn 32 positioned below the native mitral valve leaflets 12a, 12b and adjacent to the mitral valve native annulus 12c. The arrows 142 indicate the radially outward direction of balloon inflation and the resulting expansion of the stent mounted replacement heart valve 10.

Figure 7C:
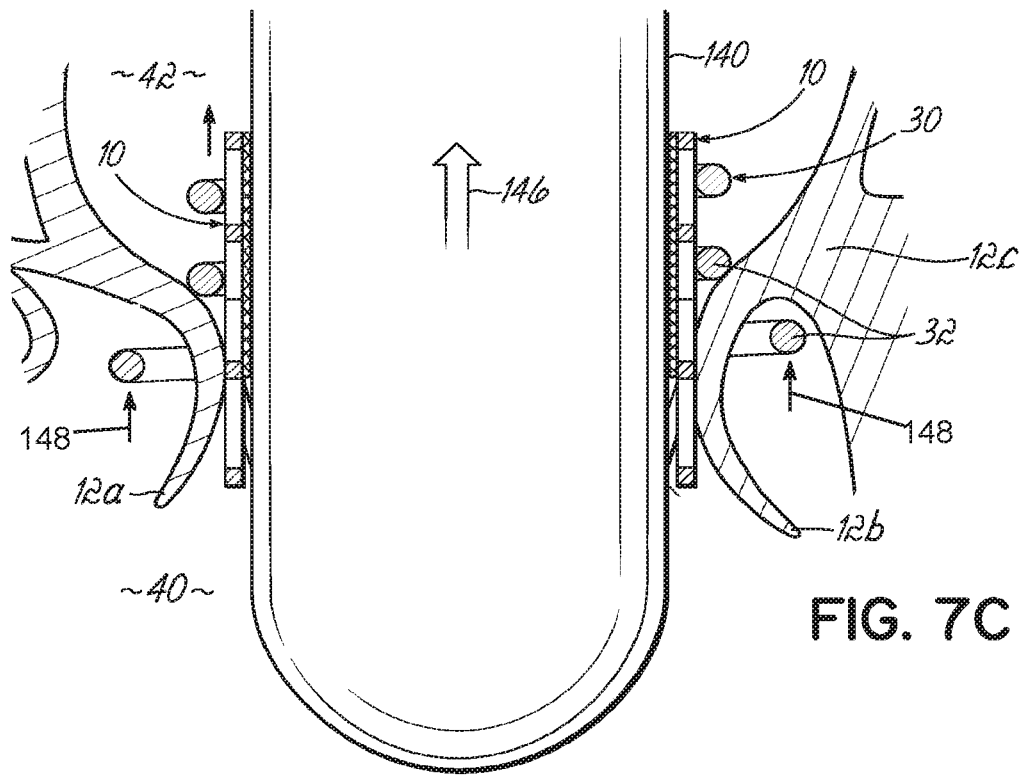
FIG. 7C illustrates a further portion of the procedure in which the stented replacement heart valve is expanded using a balloon catheter.

FIG. 7C illustrates expansion of the balloon 140 and stent mounted replacement heart valve 10. Since the diameter of the upper two coils or turns 32 of the helical anchor 30 are smaller, as the balloon 140 is expanded, the stent mounted replacement heart valve 10 first contacts the smaller turns 32 of the helical anchor 30. The stent mounted heart valve 10 becomes engaged against these two smaller diameter turns or coils 32. While in this position, the catheter deploying the balloon 140 may be used to manipulate or reposition the helical anchor 30. The movement of the balloon catheter 140, such as in the direction of the large arrow 146, will result in the large turn 32 of the helical anchor 30 being moved upwardly toward the native mitral annulus 12c in this illustrative example. That is, the turn or coil portion 32 adjacent to the native mitral annulus 12c will move in the direction of the small arrows 148 adjacent thereto. This also results in an upper movement of the turns or coil portions 32 above the native mitral valve annulus 12c. In fact, with enough force, once the turn or coil portion 32 below the annulus 12c comes in contact with the leaflet 12a or 12b or annulus tissue 12c below the mitral valve 12, the helical anchor 30 can actually be sprung open such that a segment of the helical anchor 30 that connects the turn or coil portion 32 above the leaflet 12a or 12b and below the leaflet 12a or 12b, becomes extended. This can increase the gap between segments of the helical anchor 30.

Figure 7D:
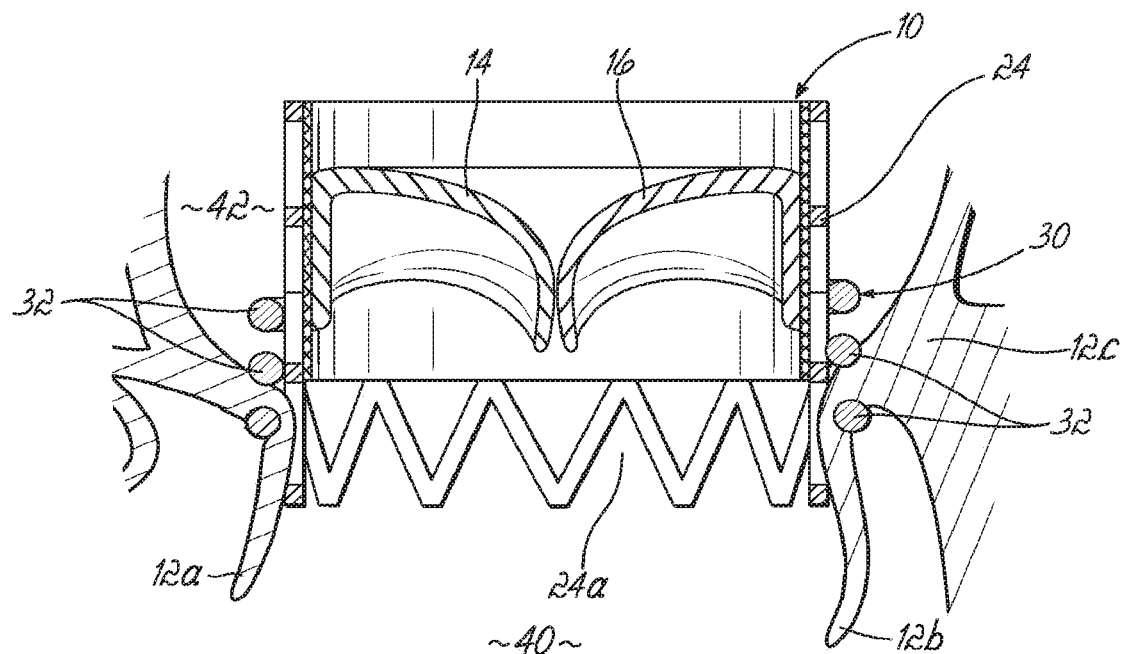
FIG. 7D is a further portion of the procedure and illustrates a cross-sectional view of the implanted replacement heart valve within the helical anchor.
Figures 1, 7D:
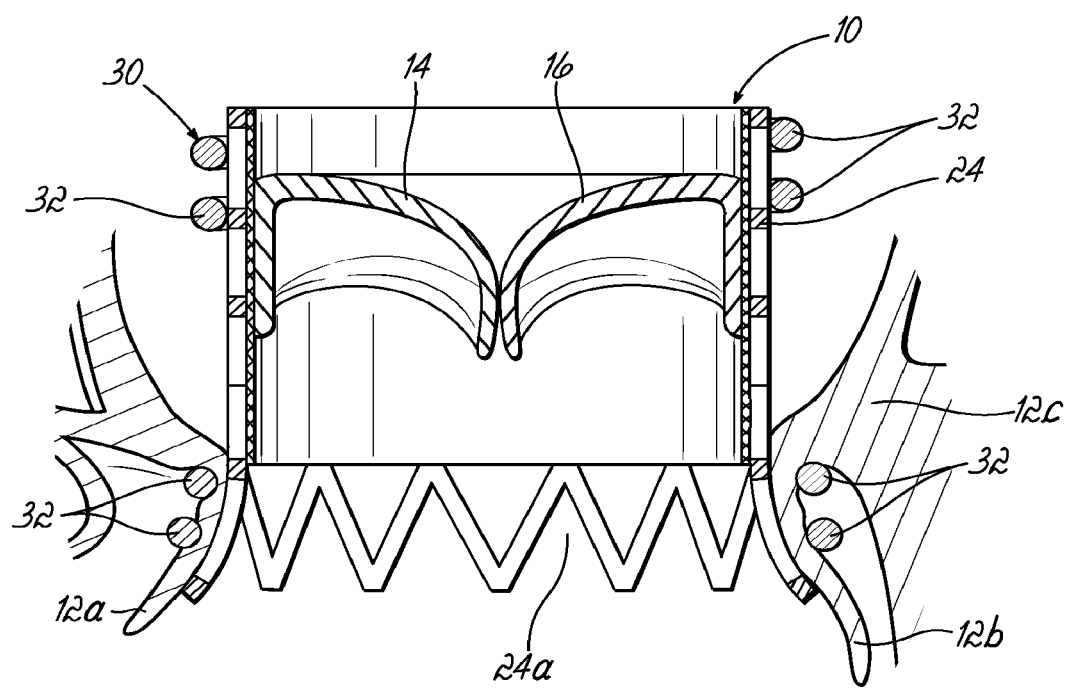

FIG. 7D illustrates a stent mounted replacement heart valve 10 fully expanded after deployment and expansion by a balloon catheter 140, which has been removed. The largest turn or coil 32 of the helical anchor 30 is positioned relatively high just under the native mitral annulus 12c. After full inflation of the balloon catheter 140, the system cannot move because the native mitral valve of leaflets 12a, 12b are now trapped between the helical anchor 30 and the stent mounted replacement heart valve 10. The balloon catheter 140 that holds the replacement heart valve 10 may be moved in any direction. In this figure, up and down motions are clearly possible as these would be made by moving the balloon catheter 140 in and out of the patient. There are many deflectable catheters which would allow the balloon catheter 140 to move laterally also.

This series of figures is intended to show how procedures can be conducted with a helical anchor 30. The anchor 30 can be engaged and manipulated by the stent mounted valve 10 prior to the final positioning and full expansion of the stent valve 10.

It is also possible to manipulate the anchor 30 prior to its release. The anchor 30 can have a catheter or other element attached to it during this procedure. So both the anchor 30 and the stent mounted valve 10 could be remotely manipulated to achieve a desired result.

FIGS. 7A-7D also show how inflating the balloon 140 inside smaller turns 32 of the anchor 30 can serve to "tighten" a larger turn 32. Part of the larger turn or coil 32 under the annulus 12c is drawn up above the annulus 12c when the smaller turn or coil 32 is expanded, thus shortening the coil 32 under the annulus 12c. This allows the large coil 32 to tighten around the stent valve 10. This effect is more pronounced when a larger coil 32 is located between two smaller coils 32 of the anchor 30. The two small coils 32 on each side of the larger coil 32 expand and thus decrease the diameter of the larger coil 32 so the larger coil 32 can trap and assist in anchoring the valve 10.

It is very important to position the anchor 30 as close to the annulus 12c as possible. This is the natural anatomic location for the valve 10. If the anchor is attached to leaflet tissue 12a, 12b remote from the annulus 12c, the leaflet tissue 12a, 12b moves with each beat of the heart. This can cause rocking of the anchor 30 and the valve 10. Repeated motion can lead to valve dislodgement. So strategies to allow placement of large coils 32 of the anchor 30 near the annulus 12c are important. It is also useful to convert a larger coil 32 to a smaller coil 32 so that the coil 32 can actually function to trap the stent valve 10.

FIG. 7D-1 illustrates another embodiment of a replacement valve 10 and helical anchor 30 combination in which the upper end of the replacement valve does not flare outward but rather is retained in a generally cylindrical shape, for example, by upper coils 32 of the anchor 30. The lower end or outflow end is flared radially outward as shown. It will be appreciated that structure, such as a seal (not shown) may be included between the stent 24 and the lower coils 32 for both sealing purposes as previously described as well as or alternatively to provide a softer, more compliant surface against the native mitral leaflets 12a, 12b. In addition, it will be appreciated that the upper coils 32 create a gap and do not engage or trap the tissue adjacent the native mitral valve in the atrium. On the other hand, the lower coils 32 engage tissue just underneath the native mitral annulus 12c. The embodiment of replacement valve 10 shown in FIG. 7D-1 stands in contrast to valves 10 configured as previously shown, such as in FIGS. 1A and 1B, in which the valve retains a cylindrical shape after implantation and application of a helical anchor 30, and, for example, that shown in FIG. 7D in which the valve 10 includes a very slight outwardly directed configuration at the lower or outflow end but does not result in any significant flare.

Figure 8C:
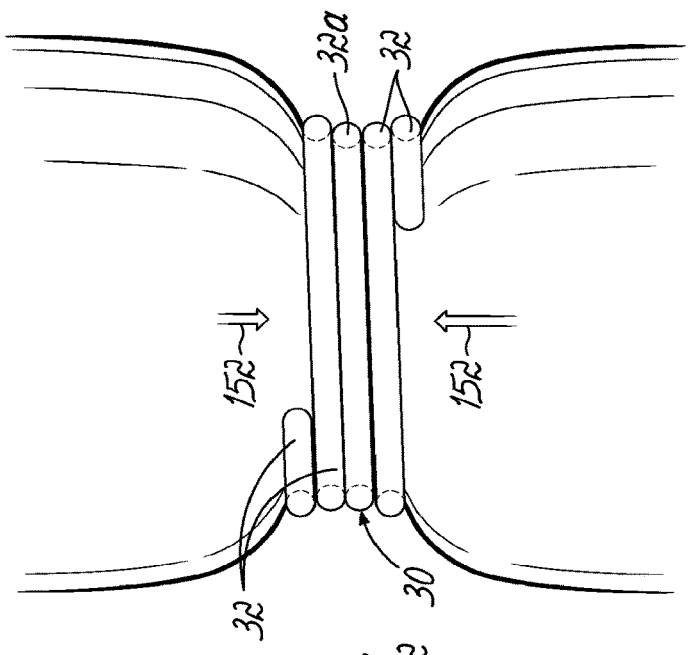
FIG. 8C is a view similar to FIG. 8B but illustrating even further expansion of the balloon catheter.
Figure 8B:
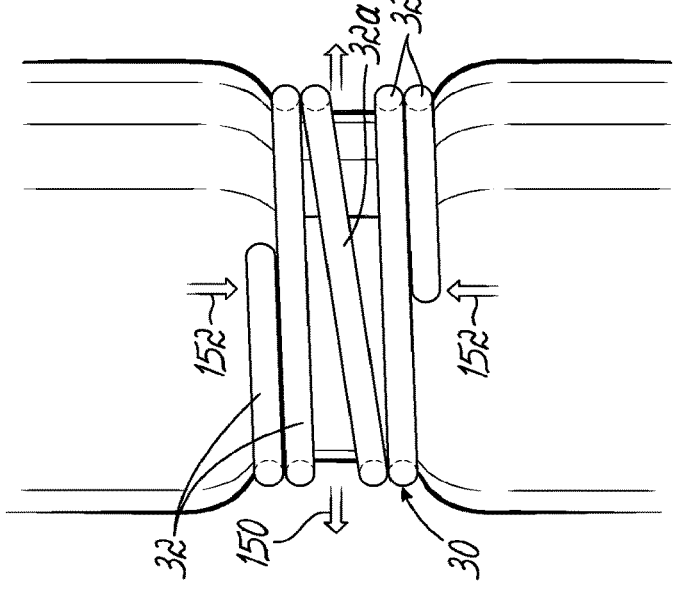
FIG. 8B is a view similar to FIG. 8A, but illustrating further expansion of the balloon catheter.
Figure 8D:
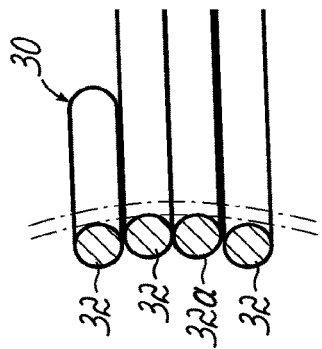
FIG. 8D is an enlarged cross-sectional view showing compression of the helical coils from FIG. 8C.
Figure 8A:
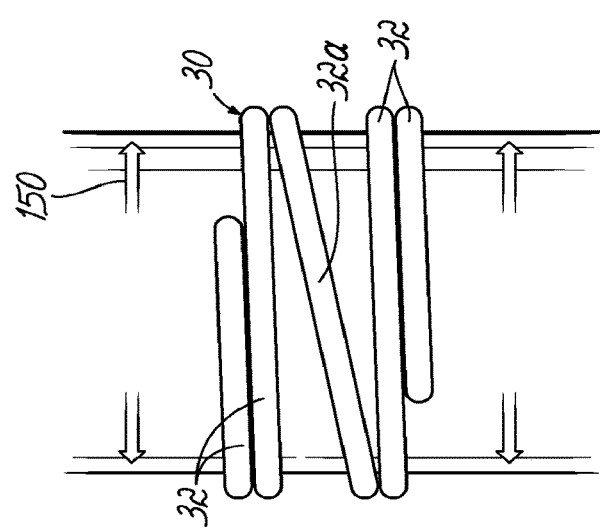
FIG. 8A is an elevational view of another embodiment of a helical anchor being expanded by a balloon catheter.

FIGS. 8A-8D illustrate the use of a balloon catheter 140 to expand a helical anchor 30 without the presence of a stent mounted replacement heart valve 10. Specifically, FIG. 8A illustrates a helical anchor 30 with approximately four coils or turns 32. There are two coils 32 on each side of a joining segment 32a which separates them to create a gap. Mitral valve native leaflets (not shown) could easily be positioned between the coils 32 at the position of the gap created by the joining segment 32a. In this figure, the balloon 140 is beginning to be expanded as shown by the radially outward directed arrows 150. FIG. 8B illustrates further expansion of the balloon 140 thereby causing the helical anchor 30 to create an indentation in the balloon 140 around the helical anchor 30. The balloon 140 on both sides of the helical anchor 30 expands further. This results in a force on the turns or coils 32 of the helical anchor 30 that moves them together generally shown by the arrows 152. As the balloon 140 is expanded further, as shown in FIG. 8C, the gap between the turns or coils 32, 32a diminishes and eventually may be completely closed such that the two main portions of the helical anchor 30 are compressed against each other in the direction of the blood flow or central axis of the helical anchor 30 (i.e., along the length of the balloon 140). FIG. 8D illustrates a cross sectional view showing the turns or coils 32, 32a of the helical anchor 30 compressed together. As shown in these figures, the coils 32, 32a of the helical anchor 30 may be compressed against each other by inflating a balloon 140 inside the helical anchor 30. There does not need to be a joining segment 32a or gap for this to occur. The helical coils 32 would be compressed tightly against each other with or without the gap illustrated in this embodiment.

This compression can serve as a "motor" to allow various functions to occur. For example, it can be possible to mount pins or fasteners (not shown) to the turns 32, 32a of the anchor 30 that can be driven and activated by the inflation of the balloon 140. The pins or fasteners could be positioned so they pass through the native valve leaflet. The fasteners could also traverse the native leaflets and move into the anchor 30 on the opposite side of the leaflet. A fabric coating, spongy coating or another receptive material on the anchor 30 would improve the retention of fasteners.

Generally, these methods and devices would allow for areas of the mitral valve 12 near the annulus 12c or on the annulus 12c to be fastened to a helical anchor 30. The fasteners could traverse the valve tissue and engage coils 32 on the one or on both sides of the leaflets. Leaflet trapping by balloon inflation can allow the mitral valve 12 and its annulus 12c to be manipulated and to perform therapeutic procedures. For example, the anchor coils 32 once fastened to a valve leaflet 12a, 12b could be reduced in size to create a purse string effect on the valve annulus 12c—resulting in an annular reduction or annuloplasty procedure. A drawstring (not shown) could be added to the anchor 30 to reduce the diameter.

The fasteners could be used to join segments of the helical anchor 30 together. For example, turns or coils 32 of the anchor 30 above the leaflet 12a, 12b could be joined together. Fabric or other material could be wrapped around or otherwise placed on the anchor coils 32 and pins or fasteners from one coil 32 could engage and trap themselves in the fabric of an adjacent coil 32. Adjacent coils 32 could engage each other. This can create a greater mass on each side of the leaflet 12a, 12b to control the mitral annulus 12c. In summary, balloon inflation inside a helical anchor 30 can drive coils 32 of the anchor 30 together. This maneuver can be used as a motor or drive mechanism to activate mechanical systems. It can also move anchor coils 32 tightly together.

FIGS. 9A-9D illustrate another ability of the helical anchor 30 as the helical anchor 30 is expanded by a balloon 140. In this regard, the actual total length of the helical coils 32 forming the anchor 30 remains the same. Therefore, to increase the diameter of the helical anchor 30, the ends 30a, 30b of the helical anchor 30 must move to accommodate the expansion. This movement may also be used as a motor or drive mechanism to activate additional functions. More specifically, FIG. 9A illustrates a balloon 140 being expanded inside the helical anchor 30. As the balloon 140 expands, the diameter of the helical anchor 30 increases and the opposite ends 30a, 30b of the helical anchor move to accommodate the expansion. As shown by the arrows 160, the ends 30a, 30b of the coils 32 move or rotate in opposite directions. FIG. 9B illustrates continuation of the balloon expansion and the previous figures of FIGS. 8A-8D show how the balloon 140 also compresses the coils 32 of the helical anchor 30 together. FIG. 9B highlights how the coils 32 of the helical anchor 30 rotate generally as the balloon 140 expands. This rotation is helpful in retaining a stent mounted replacement heart valve as the tension around the stent portion of the heart valve (not shown) increases. FIG. 9C illustrates that the helical anchor 30 has unwound as it expands under the force of the balloon 140. There are fewer turns or coils 32 and the remaining turns or coils 32 are now larger in diameter. FIG. 9D shows a cross sectional view of the expanded helical anchor 30. The motion of the ends 30a, 30b of the helical anchor 30 can be used to perform functions. As further described below, for example, the movement of the coils 32 of the helical anchor 30 may be used to drive anchors, or perform other functions.

Figure 10A:
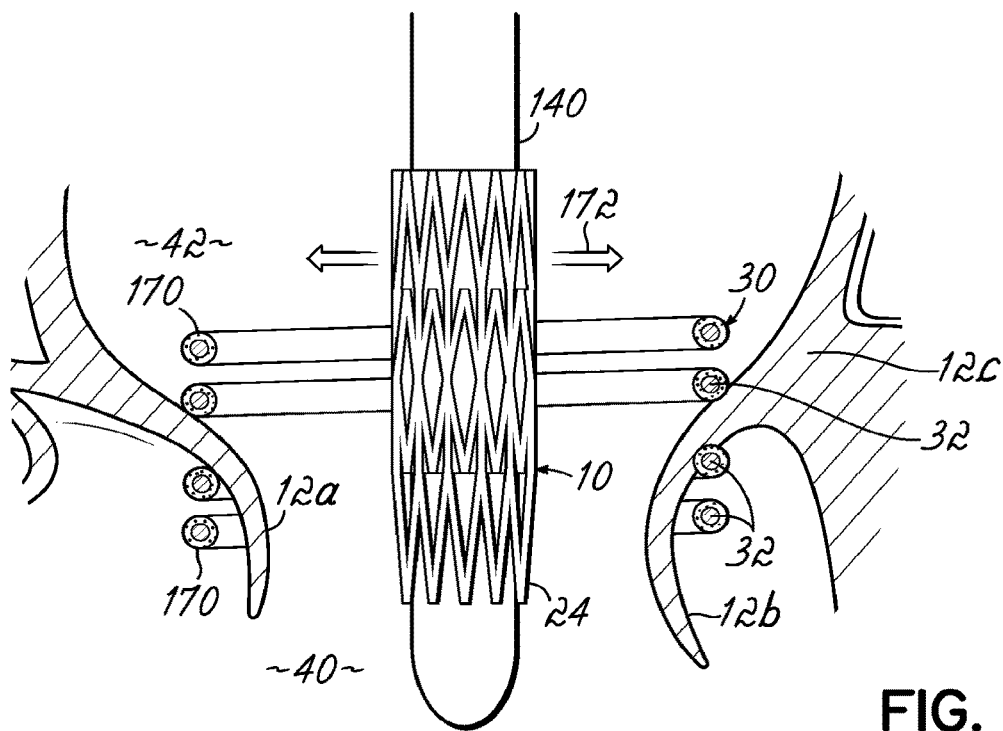
FIG. 10A is a partial cross-sectional view illustrating another embodiment of a helical anchor inserted or implanted at a native heart valve site and insertion of a stent mounted replacement heart valve within the helical anchor and native heart valve site.
Figure 10B:
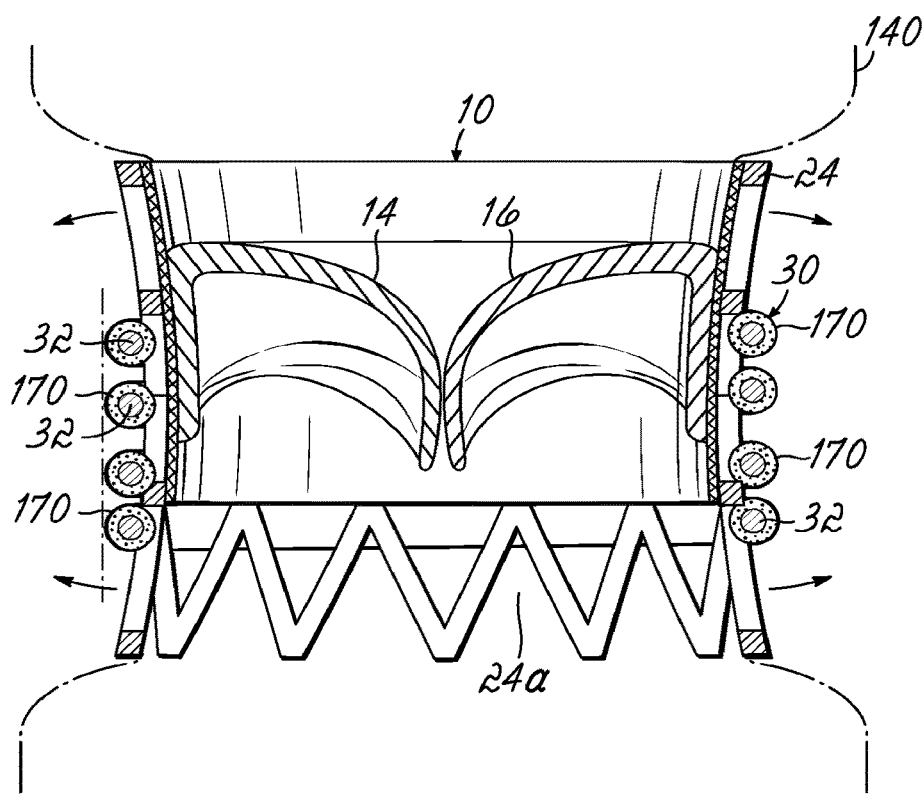
FIG. 10B is a cross-sectional view similar to FIG. 10A, but illustrating expansion and implantation of the stent mounted replacement heart valve within the helical anchor.
Figure 10C:
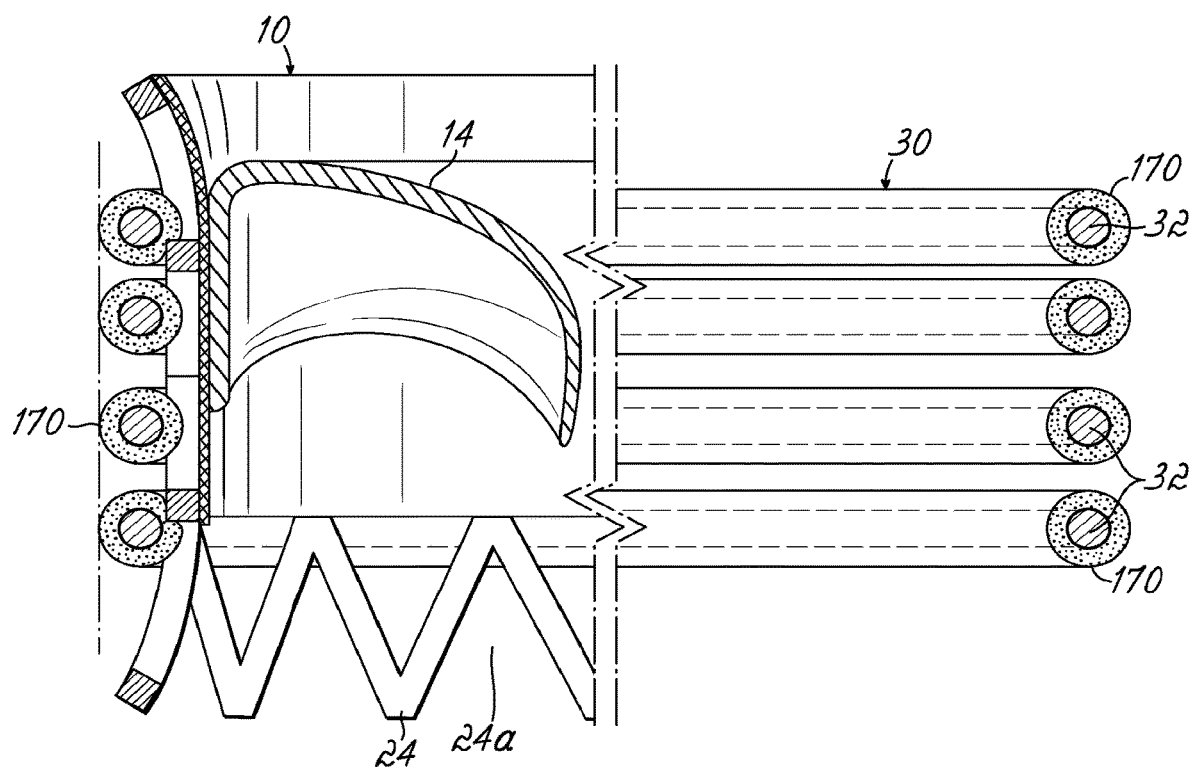
FIG. 10C is a cross-sectional view, partially fragmented, of the implanted replacement heart valve and helical anchor shown in FIG. 10B.
Figures 1, 10C:
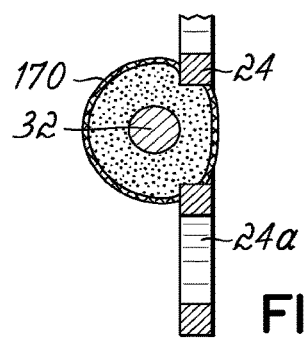
Figure 10D:
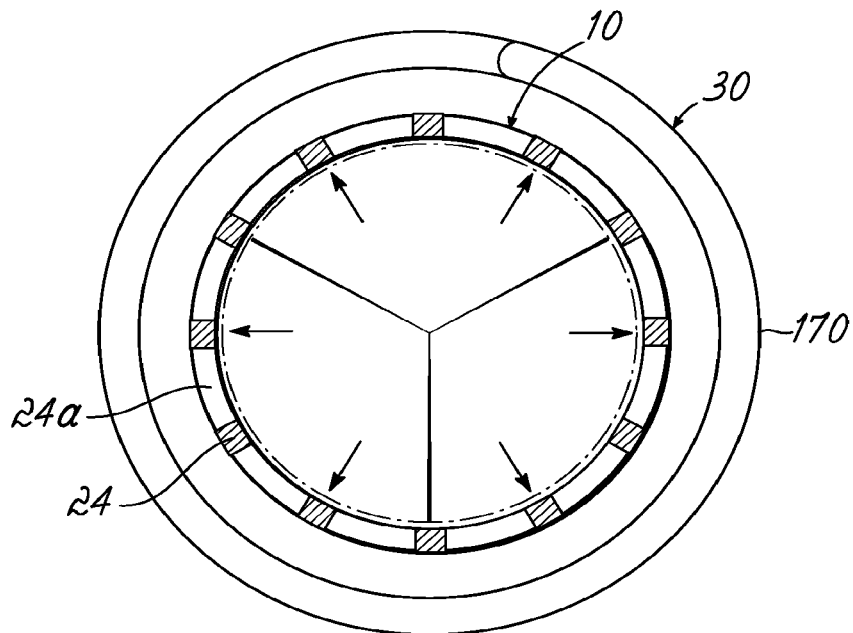
FIG. 10D is a top view illustrating the process of expanding the stent mounted replacement heart valve within the helical anchor of FIG. 10C.
Figure 10E:
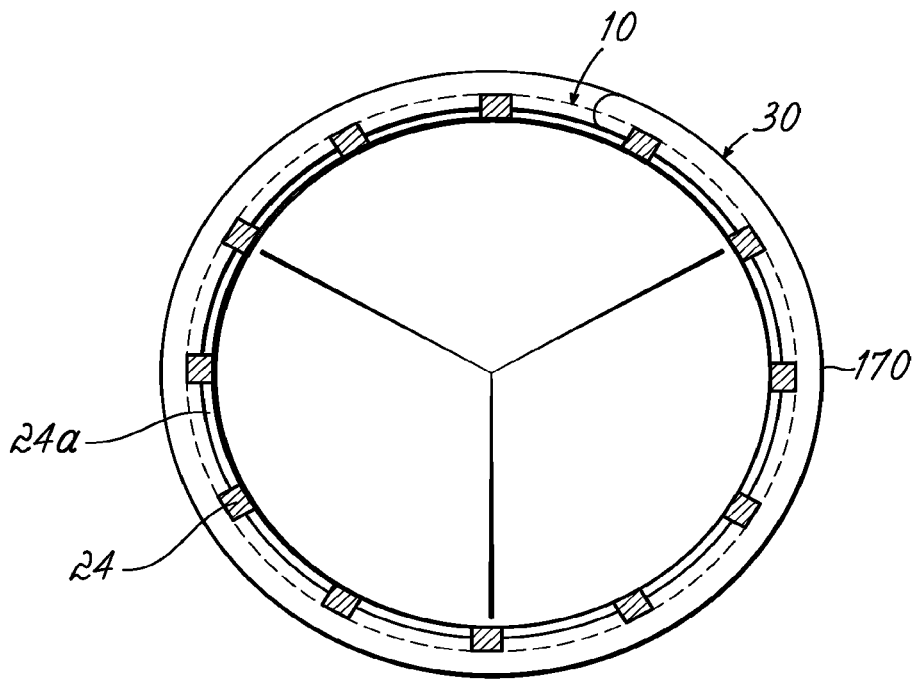
FIG. 10E is a top view similar to FIG. 10D, but illustrating full expansion and implantation of the stent mounted replacement heart valve.

FIGS. 10A-10E illustrate the effect of a cover or coating 170 on the helical anchor 30. Also, the replacement valve 10 as shown, for example, in FIGS. and 10C, takes on an outward flare at both the upper and lower ends. This may not be desirable for various reasons, but rather, at least one end of the valve 10 may be desired to have and retain a generally cylindrical cross sectional shape (as viewed from above or below). The coating or covering 170 may be in the form of any type of sheath or material applied to the helical anchor 30 and may be comprised of any biocompatible material. For example the coating 170 may be made of fabric material, such as Dacron, Teflon or other material. It may be formed from PTFE or EPTFE in fabric form that has a fabric texture or as a plastic sleeve, or cover or coating that is smooth. There may be a foam material under the coating 170 as is commonly used in, for example, surgical valves. The foam material may consist of rolls of fabric or folds of fabric. Other possible materials include resilient materials or, more specifically, material such as medical grade silicone. Biological materials may also be used, and may include animal, human, or bioengineered materials. Some materials commonly used in cardiac repair procedures are pericardium and intestinal wall materials. FIG. 10A illustrates a helical anchor 30 which is covered by a coating 170 comprised of a fabric backed by a foam material. The helical anchor is positioned inside the native mitral heart valve 12 with two turns or coils 32 above and two turns or coils 32 below the native mitral valve annulus 12c. A stent mounted replacement heart valve 10 is placed inside of the helical anchor 30 and inflation of the balloon delivery catheter 140 inside the replacement heart valve 10 has begun as indicated by the arrows 172. In FIG. 10B, the replacement stent mounted valve 10 is shown fully expanded against the helical anchor 30. Typically, the stent portion 24 of the valve 10 is comprised of thin metal material that includes openings or cells. These openings or cells become embedded against the coating or covering 170. The stent 24 therefore firmly engages with the helical anchor 30 creating a very strong attachment for the replacement valve 10 inside the helical anchor 30. FIG. 10C more specifically illustrates an enlarged view demonstrating how the stent portion 24 has deformed the fabric and foam coating 170 of the helical anchor 30. This engagement is very strong and prevents the replacement heart valve 10 from becoming dislodged. FIG. 10C-1 is an even further enlarged view showing a cell or opening 24a of the stent 24 that is engaged against the foam and fabric covering 170, creating a very strong physical connection between these two components. FIG. 10D illustrates a balloon catheter 140 expanding a replacement valve 10 inside of the coated helical anchor 30 from a view above the helical anchor 30. FIG. 10E illustrates the same view from above the helical anchor 30, but illustrating full expansion of the valve 10 after inflation of the balloon catheter 140 (FIG. 10A). The stent portion 24 of the replacement heart valve 10 is then fully engaged into the resilient, frictional coating 170 on the helical anchor 30.

FIGS. 11A-11D illustrate an embodiment that includes a covering or coating 180 on the helical anchor 30 which is intermittent, as opposed to the continuous coating 170 shown in the previous figures. In this regard, there are segments of coating 180 along the helical anchor 30 and these segments 180 may be rigidly fixed to the helical anchor 30. However, there may also be an advantage to allowing these segments 180 to slide along the helical anchor 30 as the helical anchor 30 is expanded using, for example, balloon inflation as previously described. The segments 180 may slide along the coils 32 of the helical anchor 30 to allow the helical anchor 30 to tighten and at the same time the segments 180 can firmly engage with the cells or openings 24a of the replacement heart valve stent 24.

Figure 11A:
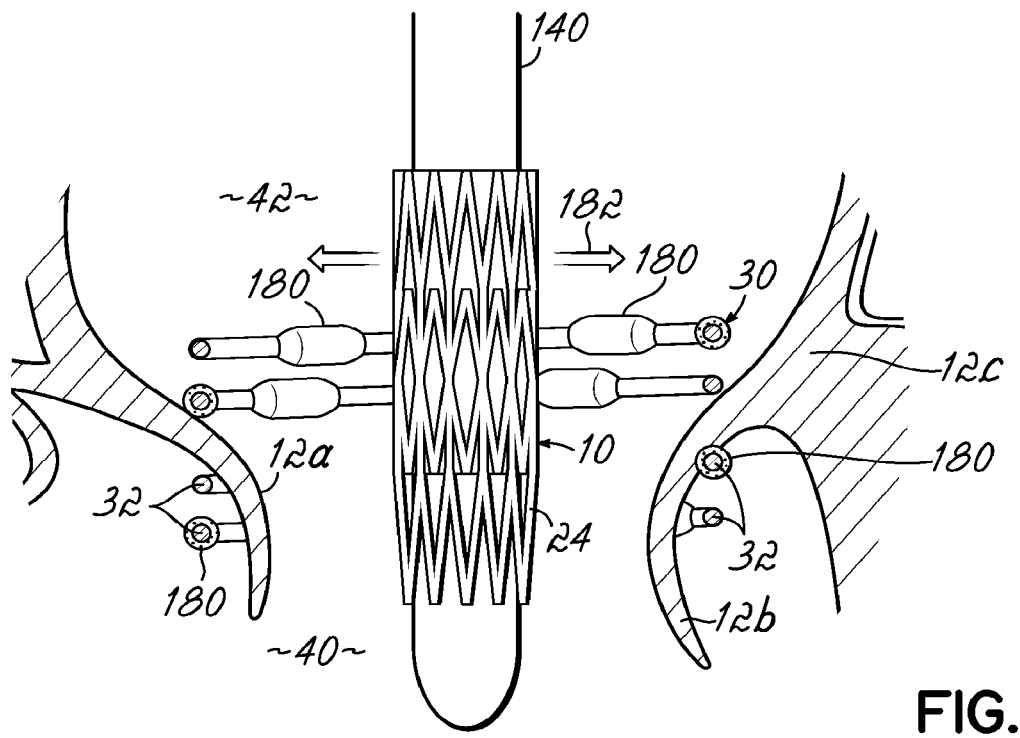
FIG. 11A is a partial cross-sectional view illustrating another embodiment of a helical anchor inserted or implanted at a native heart valve site and insertion of a stent mounted replacement heart valve within the helical anchor and native heart valve site.
Figure 11B:
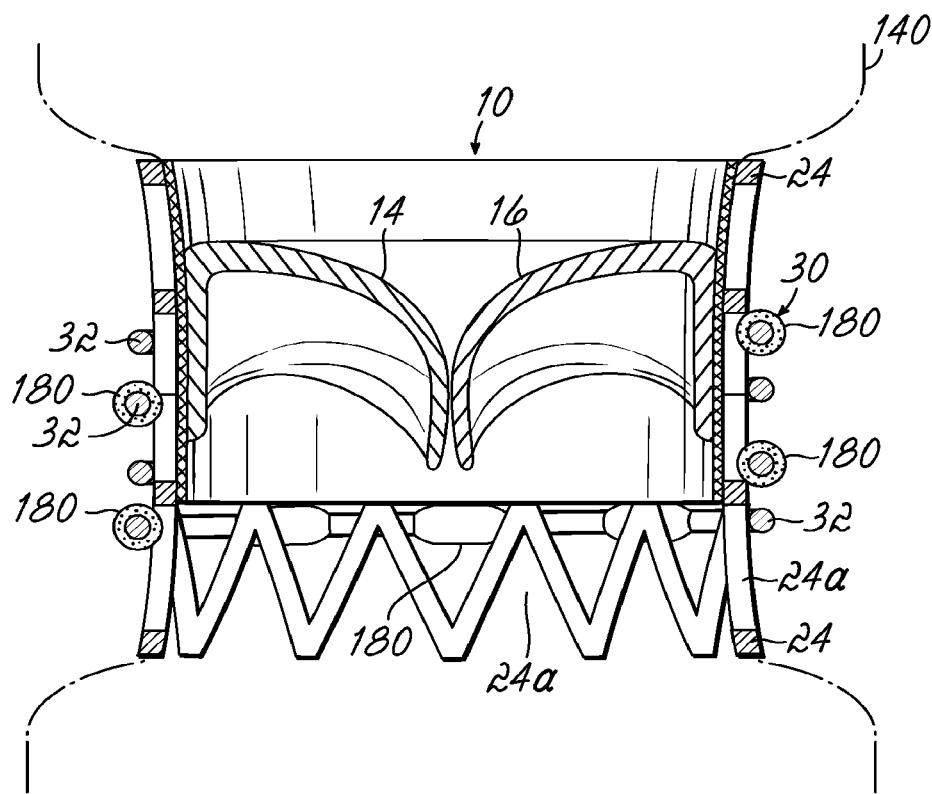
FIG. 11B is a cross-sectional view similar to FIG. 11A, but illustrating expansion and implantation of the stent mounted replacement heart valve within the helical anchor.
Figure 11C:
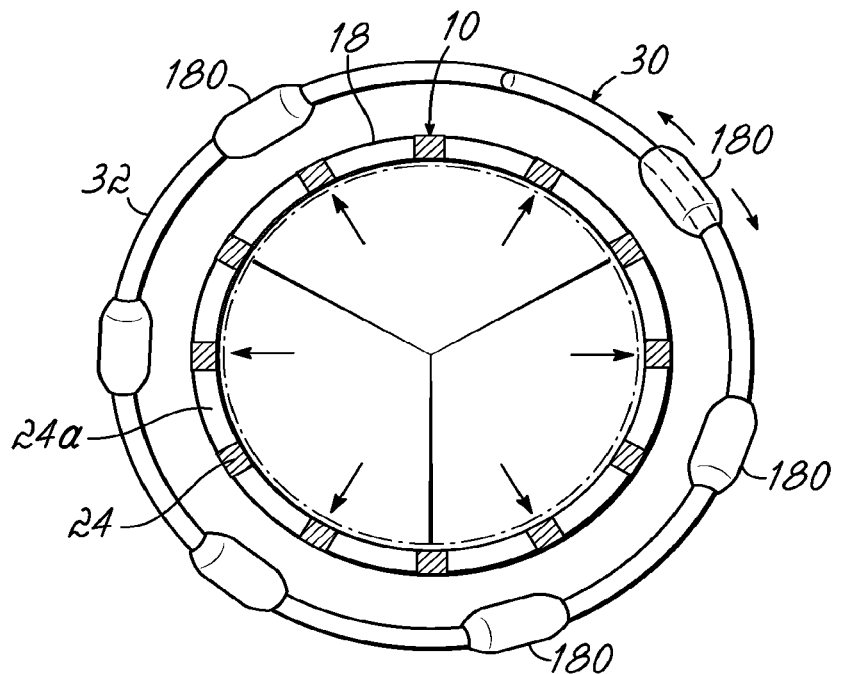
FIG. 11C is a top view illustrating the process of expanding the stent mounted replacement heart valve within the helical anchor of FIG. 11B.
Figure 11D:
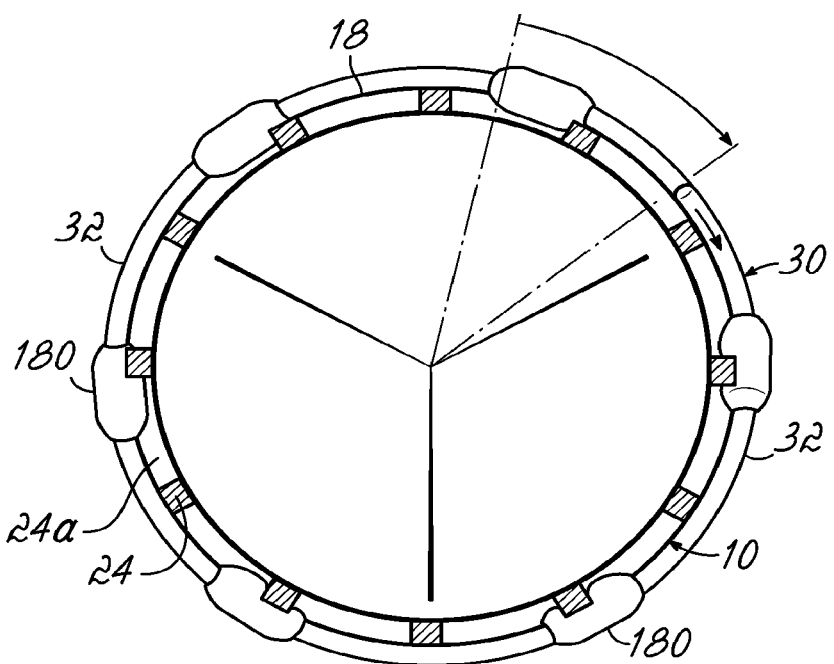
FIG. 11D is a top view illustrating full expansion of the stent mounted replacement heart valve within the helical anchor of FIG. 11C.

FIG. 11A illustrates a helical anchor 30 with a covering that is intermittent and formed with segments 180. The covering segments 180 are shown with a taper at each end to allow the anchor 30 to be turned into position without a flat leading edge to impair placement. The taper is not necessary, but assists if desired in this regard. This taper may be of any suitable design and may be angular, or curved in any shape that promotes easy motion of the helical anchor 30. A balloon catheter 140 is positioned inside of a stent mounted replacement valve 10 as previously described and is initiating its inflation as indicated by the arrows 182. FIG. 11B illustrates the stent mounted replacement heart valve 10 fully expanded. The coating segments 180 have become fully engaged within the cells or openings of the heart valve stent 24. Once these segments 180 engage with the stent 24 and enter one or more cells or openings, they become fixed to the stent 24 and they will begin to slide along the helical anchor 30. The helical anchor 30 can expand and tighten against the stent portion 24 of the replacement valve 10 and at the same time there will still be the beneficial effect of intermittent and strong attachment to the helical anchor 30 afforded by the segments 180 of high friction and resilient and/or compressible material. FIGS. 11C and 11D illustrate the process from above the helical anchor 30 showing initial expansion of the stent mounted replacement heart valve 10 in FIG. 11C and full expansion and engagement between the segments 180 and the stent 24 in FIG. 11D firmly attaching these two structures together during the implantation procedure within a patient.

Figure 12A:
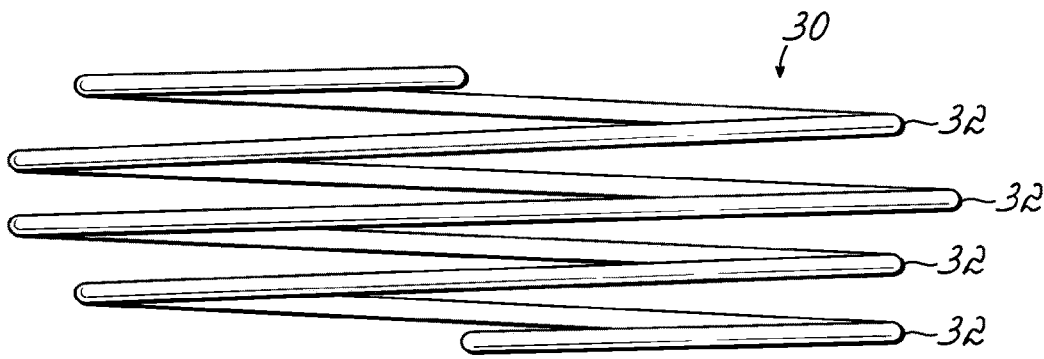
FIG. 12A is an elevational view of another embodiment of a helical anchor.
Figure 12B:
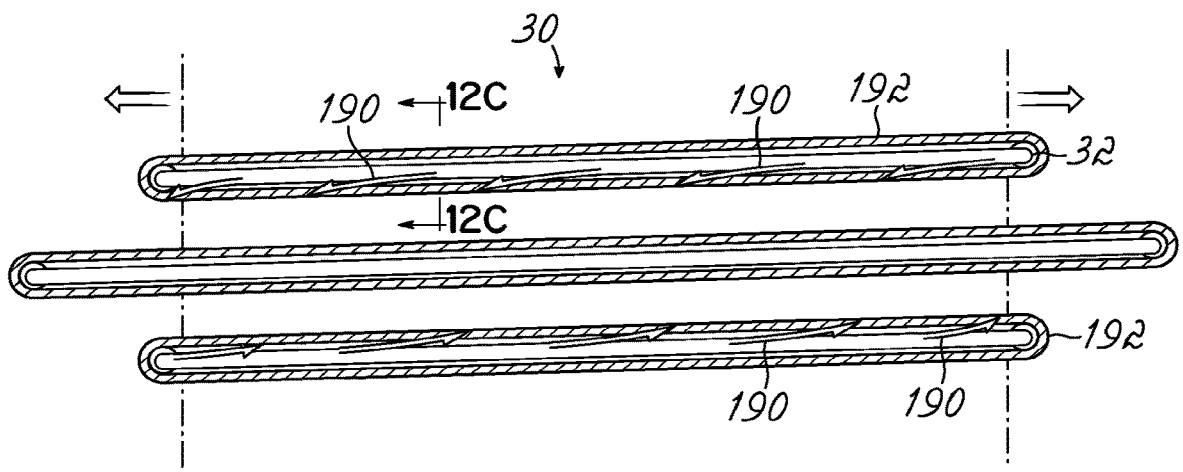
FIG. 12B is a cross-sectional view of another embodiment of a helical anchor.
Figure 12C:
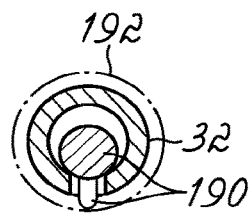
FIG. 12C is an enlarged cross-sectional view of the helical anchor taken along line 12C-12C of FIG. 12B.
Figure 12D:
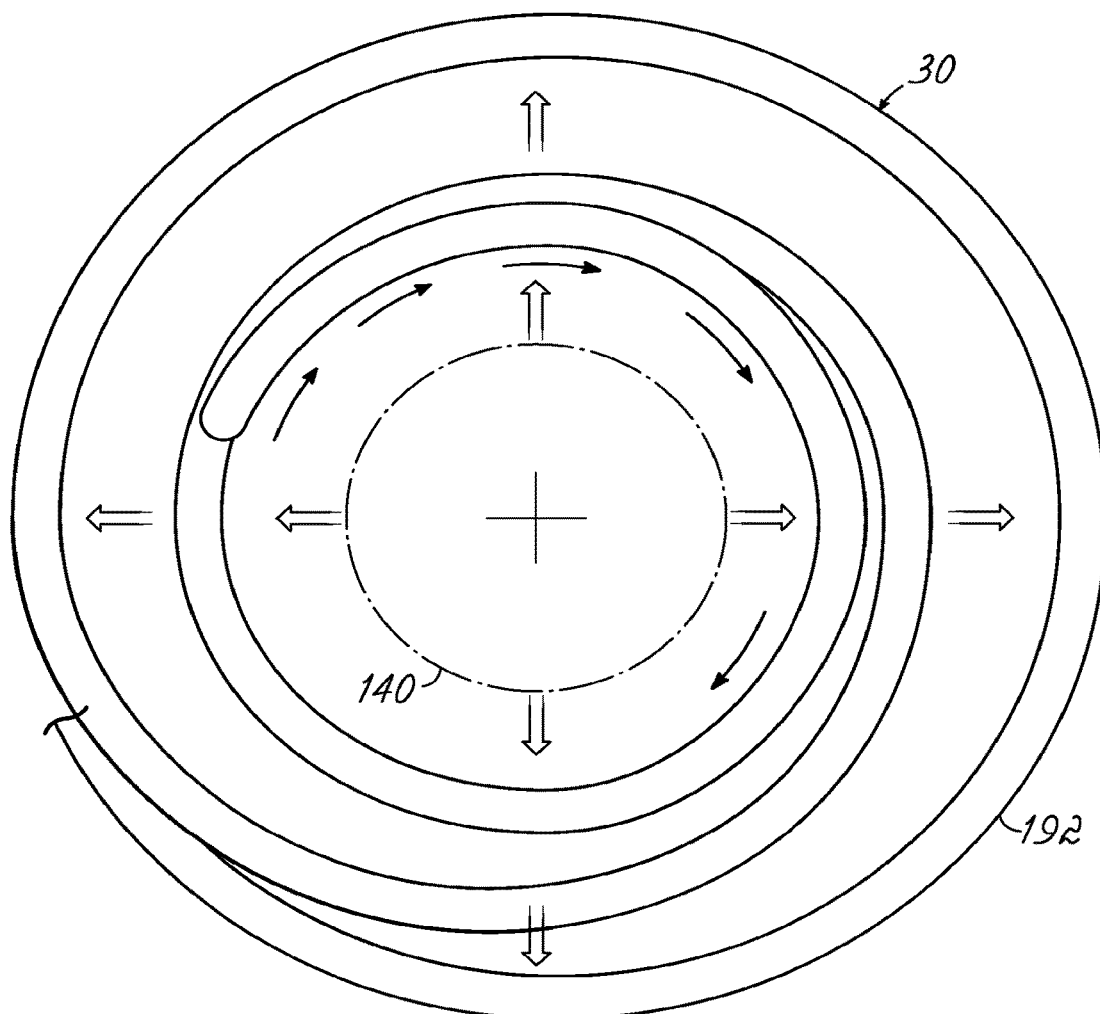
FIG. 12D is a top view of a helical anchor schematically illustrating expansion by a balloon catheter.
Figure 12E:
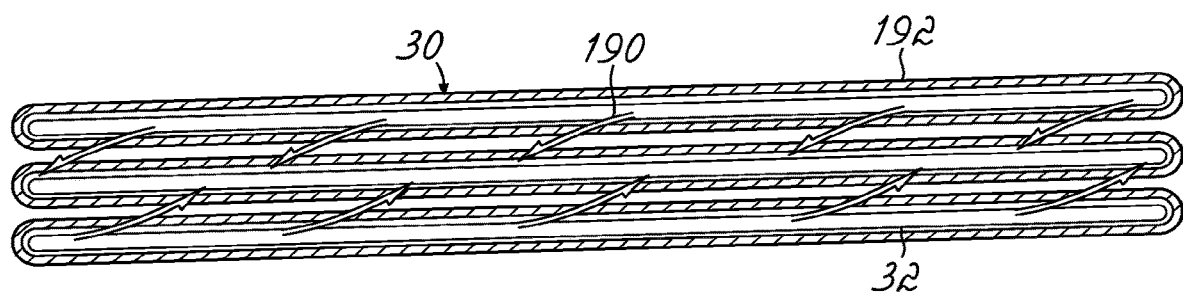
FIG. 12E is a cross-sectional view of the helical anchor shown in FIG. 12D, but expanded to show deployment of the parts into the fabric seal.

FIGS. 12A-12E illustrate a helical anchor 30 and the motor or drive function provided when the helical anchor 30 expands and the ends 30a, 30b of the coils 32 move. FIG. 12A illustrates a helical anchor 30 with about four turns or coils 32, while FIG. 12B illustrates a helical anchor 30 with about three turns or coils 32. As further shown in FIG. 12B the helical anchor 30 is attached to barbed fasteners 190 for delivery into a replacement heart valve 10. A fabric or other material coating or exterior 192 is applied around the barbs 190 and around the helical anchor 30. When a balloon 140 is inflated inside of the helical anchor 30, the two ends 30a, 30b of the helical anchor 30 move in opposite directions as the helical anchor 30 is expanded. In this manner, the barbs 190 are oriented in opposite directions to the movement of the helical anchor 30 so that these barbs 190 will be activated or move when the helical anchor 30 is expanded. FIG. 12C illustrates a cross section of the helical anchor 30 with the fabric or other covering or coating 192 and a fastener system 190 coupled with the helical coil 30. It was previously described as to how the turns or coils 32 of the helical anchor 30 may be driven together by inflation of a balloon 140. Balloon inflation also drives or moves the turns 32 of the helical anchor together, increasing the penetration of the barbs 190. The barbs 190 in FIGS. 12B-12E are oriented obliquely relative to the central axis of the helical anchor 30, however, the barbs 190 may instead deploy in a straight or parallel direction relative to the axis of the helical anchor 30, straight toward an adjacent turn or coil 32 of the helical anchor 30, driven by the compression of the helical coils 32 together by the inflating balloon 140. With expansion, the ends 30a, 30b of the helical anchor 30 move considerably, but the central part of the anchor 30 does not turn or rotate considerably. Barbs 190 without an oblique orientation may be preferred at the center coils 32. The angle of the barbs 190 may increase and their length can be increased in areas toward the ends 30a, 30b of the helical anchor 30 where the movement during inflation of a balloon 140 is more pronounced. FIG. 12D illustrates a top view of the helical anchor 30. As the balloon catheter 140 is inflated, the helical anchor 30 increases in diameter and the ends 30a, 30b of the helical anchor rotate to allow this diameter expansion. As shown in FIG. 12E, the expansion of the helical anchor 30 has mobilized or deployed the barbs 190 and the barbs 190 engage into the fabric or other material coating 192 within the middle or central turn or coil 32. This locks the turns or coils 32 of the helical anchor 30 together. No native valve leaflet tissue is shown in FIG. 12E, however, it will be appreciated that leaflet tissue could be located between the turns or coils 32 and the barbs 190 could entail and engage the leaflet tissue for further securing the helical anchor 30 to the native mitral valve tissue.

Figure 13A:
FIG. 13A is an elevational view of another embodiment of a helical anchor.
Figure 13B:
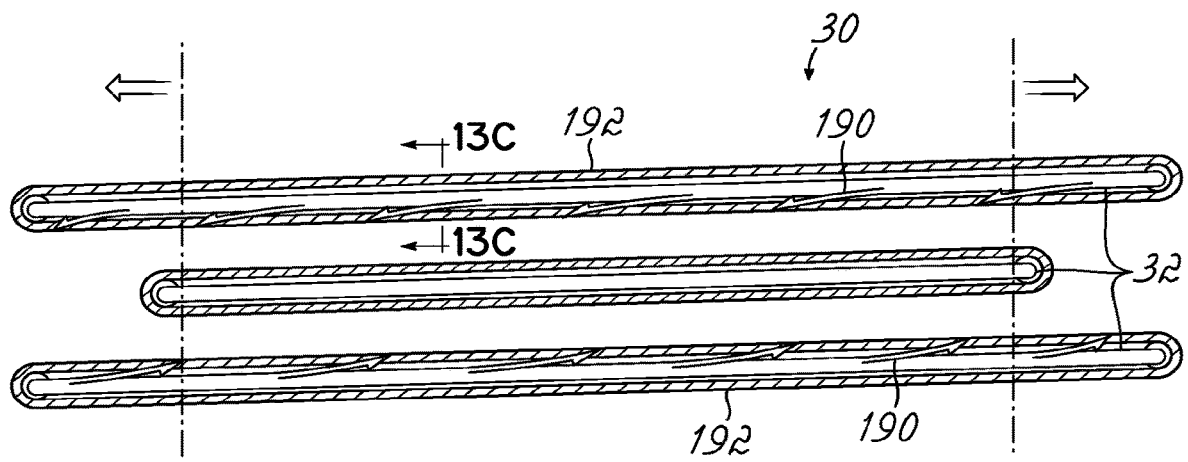
FIG. 13B is a cross-sectional view of another embodiment of a helical anchor.
Figure 13C:
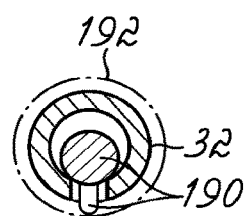
FIG. 13C is an enlarged cross-sectional view of the helical anchor taken along line 13C-13C of FIG. 13B with deployment of the barbs into the outer seal layer.

FIGS. 13A-13C illustrate another embodiment in which a helical anchor is used having relatively larger diameter turns or coils 32 at the ends of the anchor 30 and a relatively smaller turn or turns in a middle or central portion of the helical anchor 30. The helical anchor 30 is attached to barbs 190 and covered by a suitable coating material 192, such as fabric or other material. When the balloon 140 is inflated the ends of the helical anchor 30 begin to move and the barbs 190 are activated as the central, smaller helical turn 30 is expanded outwardly. This particular arrangement is ideal to attach to the native mitral valve of a patient. One barbed turn or coil 32 of the helical anchor 30 may be placed above the native mitral valve leaflets and one barbed turn or coil 32 may be placed below the native mitral valve leaflets. The smaller diameter turn or coil 32 may sit above or below the native mitral valve leaflets. When the balloon (not shown) is inflated, the large helical turns or coils 32 above and below the native mitral valve leaflets will be driven towards each other as generally shown and described above in FIGS. 8A-8D. Also, the anchor ends will rotate and barbs 190 will deploy through the mitral valve leaflet tissue positioned between the larger turns or coils 32 close to the native annulus. The two large helical turns or coils 32 can also be bound together as the barbs 190 cross the mitral tissue and penetrate the covering 192 on the helical coil 32 at the opposite side of the native mitral valve. These actions will trap the mitral valve between the turns or coils 32 of the helical anchor 30, although it is not necessary for this to occur. It is also apparent that the large diameter turns or coils 32 at the opposite ends of the helical anchor 30 will become smaller in diameter as the balloon is expanded. In this regard, the upper and lower turns or coils 32 "donate" to the middle coil or turn 32. This will result in a diameter reduction for the upper and lower coils 32. After the coils 32 have been fastened to the native mitral valve perimeter or annulus, this will result in a downsizing of the diameter of the mitral valve, i.e., an annuloplasty procedure will result. When the barbs 190 are retained in the native mitral valve tissue firmly, they should not dislodge or withdraw after penetration. FIG. 13C illustrates a cross sectional view of a helical anchor 30 from FIG. 13B, as well as a barb system 190 and coating 192, such as fabric or other material. As described previously, barbs 190 can deploy directly from the helical anchor 30 at a roughly 90° angle relative to the coil 32. This may be driven simply by compressing coils 32 relative to one another as described above in connection with FIGS. 8A-8D. The movement of the helical coil or anchor turns 32 longitudinally or rotationally also allows barbs 190 or other types of fasteners to be applied in a direction which is more parallel or oblique relative to the turns or coils 32 of the helical anchor 30.

Figure 14A:
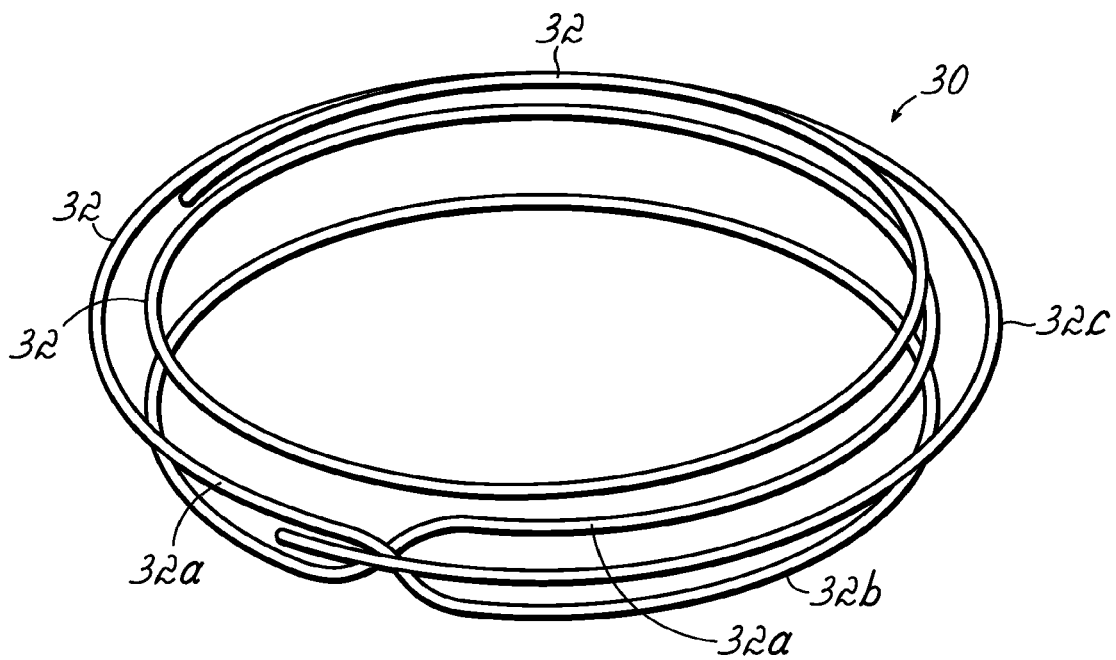
FIG. 14A is a perspective view of an alternative helical anchor.
Figure 14B:
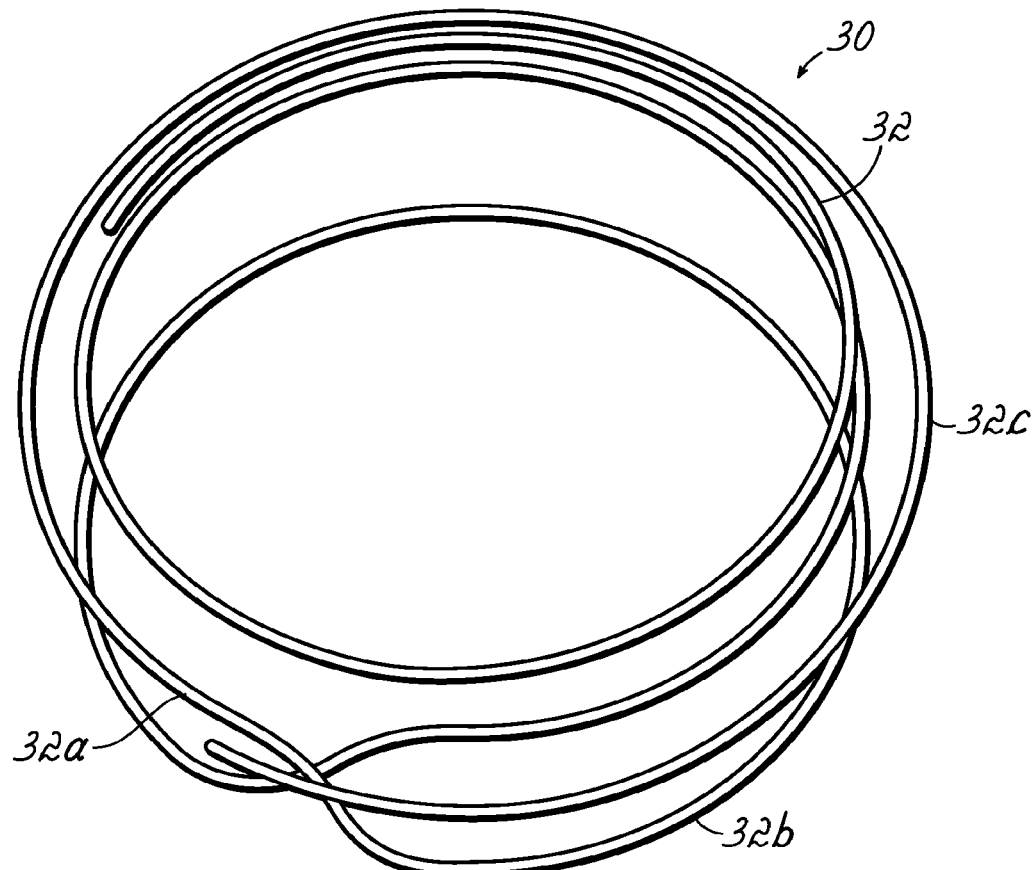
FIG. 14B is a top perspective view of the helical anchor shown in FIG. 14A.
Figure 14C:
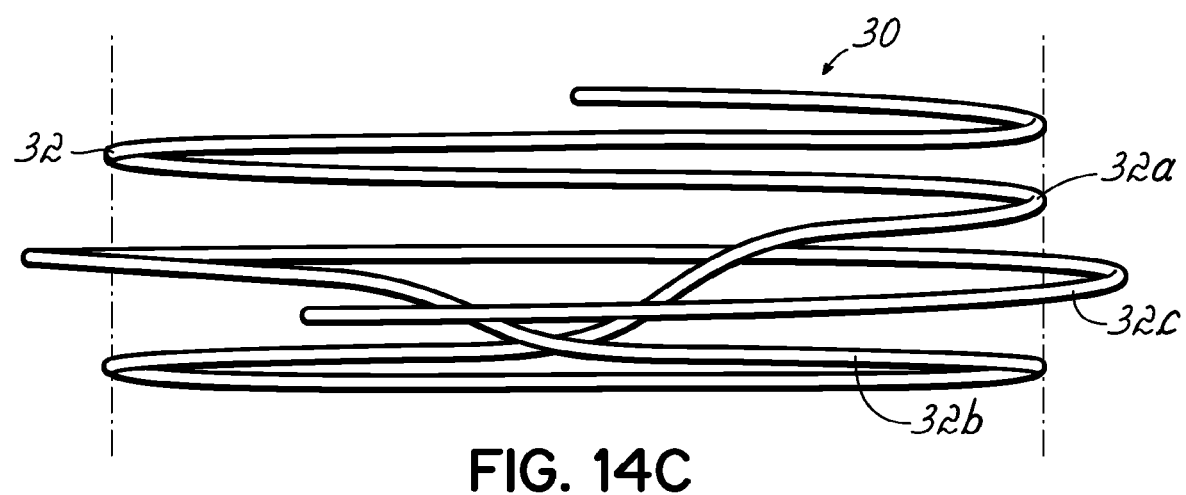
FIG. 14C is a front view of the helical anchor shown in FIGS. 14A and 14B.

FIGS. 14A-14C illustrate a different configuration for a helical anchor 30. This anchor 30 has generally four coils 32. There are two upper coils 32 followed by a joining segment 32a (gap segment). The joining segment 32a is typically used to separate the coils 32 of the anchor 30 that sit above the valve leaflets from those that are below (in the atrium and in the ventricle, respectively). There is a coil 32b of similar size as the two upper coils 32 at the end of the joining segment 32a. This is the lowest coil 32b on the anchor 30. The final coil 32c changes direction—instead of continuing on downward, it coils back up and overlaps or crosses over an adjacent coil 32 of the anchor 30. This coil 32c is shown as the "larger convolution" in FIG. 14B. The figure shows a directional change (like the joining segment) in the anchor 30 that allows the final coil 32c to be directed upward. The final coil 32c is also larger to allow it to sit on the outside of the other coils. This larger coil 32c is the middle coil of the anchor 30 but is actually turned into the native valve first when being delivered. The important feature of this anchor 30 is that as it is turned into position, the upward bend in the joining segment 32a forces the anchor up toward the annulus. This anchor 30, when positioned with two coils above and two coils below the leaflets, sits with the larger coil 32c of the anchor 30 sitting right under the mitral valve annulus. The anchor 30 does not tend to fall into the ventricle. The lowest coils do not necessarily have to cross on the same point when viewed from the side (producing an X). They could cross for example on opposite sides.

The key element in the embodiment of FIGS. 14A-14C is for the turning of the anchor 30 into position to result in an upward motion of the end of the anchor which drives the anchor 30 into position right under the mitral valve. As this anchor is "screwed in" the lowest coil 32b forces the anchor 30 upward against the mitral annulus. The larger diameter coil 32c in the middle of the anchor 30 also helps the anchor 30 positioning right under the leaflets and close to the annulus. The mitral annulus has a certain diameter and by matching this diameter with the diameter of the largest anchor coil 32c, the anchor 30 is able to sit right under the annulus. If this coil 32c is too small, the anchor 30 can drag against the leaflet tissue and inhibit the anchor 30 from riding upward toward the annulus as it is placed. It will be appreciated that crossing coils 32a, 32b in an anchor 30 may also be useful for valve anchoring when using an anchor 30. The crossing coil 32a occurs in the lowest coil of this anchor 30. But a crossing segment 32a could occur in any location. It could occur at the top, in the middle or at the bottom of the anchor 30. The amount of crossover could also vary. Here the cross over includes the lowest two coils 32. There could be more coils that overlap. FIG. 14C shows the overlapping coil 32a with the lowest coil being outside the prior coils. The overlapping coil 32a or crossing segment could occur inside the prior coils. FIG. 14C also shows an abrupt change in pitch to cause an overlap. The overlap can also occur with a gentle change of pitch. In FIGS. 14A through 14C, the spacing between coils in both the top to bottom and side to side dimensions are exaggerated for clarity. The coils will apply compression from the top and bottom toward the center.

A major advantage of the configuration shown in FIGS. 14A-14C is that the number of coils 32 available to attach the valve is increased, but the length of the anchor 30 does not increase. This allows a shorter anchor. For example, it may be useful to have less anchor length positioned in the left ventricle 40 so the valve 10 can sit more towards the atrium 42. The overlapping or crossing coils 32a may crossover in a desired manner and allow the valve 10 to be retained with strong force and a shorter overall length inside the left ventricle 40. The overlap 32a in the anchor could also be positioned at the level where the native leaflets 12a, 12b are sitting. This would increase the trapping of the leaflets 12a, 12b—the anchor 30 could be positioned such that overlapping coils had leaflet between them. If the gap between the coils 32 of the anchor 30 were sufficiently small, the leaflets 12a, 12b could be trapped between the coils 32 without the need for additional fasteners. This arrangement may also position the leaflets 12a, 12b to be fastened to the anchor 30 or an anchoring system attached or guided by the anchor 30. This particular anchor arrangement is also useful because the lowest coil of the anchor coils 32 extends in the opposite direction to the remainder of the anchor 30—while the other coils 32 are biased downward, this is biased upward. As this anchor 30 is turned into position, the lowest coil 32b will tend to move back upward. This is actually creating a virtual reverse thread. A typical helical anchor is screwed into the valve leaflets 12a, 12b like a corkscrew and as it is turned, it moves downward. With this configuration, once the first coil of the anchor 30 is turned into the valve 12 and the joining segment 32a is reached, the anchor 30 actually begins to turn upward instead of downward as the lowest coil 32b is being turned in. This means this particular anchor arrangement will tend to sit right under the annulus 12. This is useful in optimally positioning the anchor 30 close to the underside of the annulus 12. An anchor 30 attached to the leaflets 12a, 12b away from the annulus 12 will tend to move and rock as the heart contracts. This is because of leaflet motion away from the annulus 12 as the heart beats. In contrast the annulus 12 itself moves very little as the heart beats. By placing the anchor 30 closer to the annulus 12 (away from the leaflets), the amount of movement of the anchor 30 is reduced. Each day the heart beats about 100,000 times. This repetitive motion will produce a risk of anchor and valve dislodgement. Thus minimizing the motion by placing the anchor 30 close to the annulus 12 will reduce the risk of valve implant failure. In FIGS. 14A-14C, the crossing points for the anchor coils 32 are both on the same side of the anchor 30. This creates an X. It is not necessary for the crossing points to occur at the same side. For example, they could be on opposite sides of the anchor 30.

While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in any combination depending on the needs and preferences of the operator. This has been a description of the present invention, along with the preferred methods of practicing the present invention as currently known. However, the invention itself should only be defined by the appended claims.

What is claimed is:

1. An anchor for docking a prosthetic heart valve at a native heart valve, the anchor comprising:
   a first free end and a second free end spaced axially apart from each other relative to a central axis of the anchor;
   at least three revolutions extending helically around the central axis of the anchor; and
   a covering surrounding each revolution of the at least three revolutions such that adjacent revolutions are spaced apart by the covering, and wherein the covering comprises a fabric material and a foam underneath the fabric material.

2. The anchor of claim 1, wherein the covering comprises ePTFE.

3. The anchor of claim 1, wherein the covering is fixed to the at least three revolutions.

4. The anchor of claim 1, wherein each revolution of the at least three revolutions is spaced apart from an adjacent revolution of the at least three revolutions by two layers of the covering.

5. The anchor of claim 1, wherein the covering surrounds each revolution such that it extends around a central axis of the at least three revolutions, and wherein the central axis of the at least three revolutions extends helically around the central axis of the anchor.

6. The anchor of claim 1, wherein the first end of the anchor is configured to be positioned above an annulus of the native heart valve and the second end of the anchor is configured to be positioned below the annulus of the native heart valve.

7. The anchor of claim 1, wherein the covering is configured to engage with a radially expansible prosthetic heart valve when the radially expansible prosthetic heart valve is expanded within the at least three revolutions, and wherein when the radially expansible prosthetic heart valve is expanded within the at least three revolutions, leaflets of the native heart valve are trapped between one or more revolutions of the at least three revolutions and the radially expansible prosthetic heart valve.

8. An anchor for docking a prosthetic heart valve at a native heart valve, the anchor comprising:
   a first free end and a second free end arranged opposite the first free end, the first free end and the second free end configured to be positioned axially apart, relative to a central axis of the anchor, on opposite sides of an annulus of the native heart valve;
   at least three revolutions; and
   a cover surrounding each of and spacing apart at least two adjacent revolutions of the at least three revolutions, where the cover comprises:
      a first layer comprising a fabric material; and
      a second layer comprising a foam material, wherein the second layer is disposed underneath the first layer and around at least the portion of the at least three revolutions.

9. The anchor of claim 8, wherein the cover extends along a length of the at least two adjacent revolutions of the at least three revolutions, wherein a direction of the length of the at least two adjacent revolutions extends helically around the central axis of the anchor.

10. The anchor of claim 8, wherein the cover comprises ePTFE.

11. The anchor of claim 8, wherein the anchor further comprises a joining segment disposed between two adjacent revolutions of the at least three revolutions, and wherein the joining segment creates a gap between the two adjacent revolutions in a direction of the central axis of the anchor.

12. The anchor of claim 8, wherein the at least three revolutions include a first revolution, a second revolution, and a third revolution, the second revolution disposed between the first revolution and the third revolution, and wherein a diameter of the first revolution is larger than a diameter of the second revolution.

13. An anchor for docking a prosthetic heart valve at a native heart valve, the anchor comprising:

at least three revolutions extending helically around a central axis of the anchor and configured for surrounding native leaflets of the native heart valve;

a first free end and a second free end, wherein the first free end is configured to be arranged on an atrial side of the native heart valve and the second free end is configured to be arrange on a ventricular side of the native heart valve; and a covering surrounding at least a portion of the at least three revolutions, wherein the covering spaces apart, in a direction of the central axis, at least two adjacent revolutions of the at least three revolutions, and wherein the covering is fixed to at least the portion of the at least three revolutions, and wherein the covering comprises:

a first layer comprising a fabric material; and a second layer disposed underneath the first layer and around at least the portion of the at least three revolutions, wherein the second layer is thicker than the first layer.

14. The anchor of claim 13, wherein the covering comprises ePTFE.

15. The anchor of claim 13, wherein the second layer comprises a foam material.

16. The anchor of claim 13, wherein the at least three revolutions include an upper revolution, a lower revolution, and a middle revolution, the middle revolution disposed between the upper revolution and the lower revolution, and wherein in a relaxed state, the middle revolution has a first diameter and the lower revolution has a second diameter which is larger than the first diameter.

17. The anchor of claim 16, wherein the middle revolution is configured to expand from the first diameter to a third diameter upon application of an outward radial force by radial expansion of a radially expansible prosthetic heart valve inside the anchor.

18. The anchor of claim 16, wherein the anchor further comprises a joining segment disposed between the upper revolution and the middle revolution, and wherein the joining segment creates a gap between the upper revolution and the middle revolution in a direction of the central axis of the anchor, and wherein the upper revolution is configured to be positioned on the atrial side of the native heart valve and the lower revolution is configured to be positioned on the ventricular side of the native heart valve.

* * * * *